US009783468B2

(12) United States Patent
Wang et al.

(10) Patent No.: US 9,783,468 B2
(45) Date of Patent: Oct. 10, 2017

(54) METHOD FOR PRODUCING AN AROMATIC HYDROCARBON WITH AN OXYGENATE AS RAW MATERIAL

(71) Applicants: CHINA PETROLEUM & CHEMICAL CORPORATION, Beijing (CN); SHANGHAI RESEARCH INSTITUTE OF PETROCHEMICAL TECHNOLOGY, SINOPEC, Shanghai (CN)

(72) Inventors: Zheming Wang, Shanghai (CN); Weimin Yang, Shanghai (CN); Xiqiang Chen, Shanghai (CN); Jingxian Xiao, Shanghai (CN); Feng Xu, Shanghai (CN)

(73) Assignees: CHINA PETROLEUM & CHEMICAL CORPORATION, Beijing (CN); SHANGHAI RESEARCH INSTITUTE OF PETROCHEMICAL TECHNOLOGY, SINOPEC, Shanghai (CN)

( * ) Notice: Subject to any disclaimer, the term of this patent is extended or adjusted under 35 U.S.C. 154(b) by 255 days.

(21) Appl. No.: 14/528,637

(22) Filed: Oct. 30, 2014

(65) Prior Publication Data

US 2016/0122256 A1    May 5, 2016

(51) Int. Cl.
*C07C 15/08* (2006.01)
*C07C 7/04* (2006.01)
(Continued)

(52) U.S. Cl.
CPC .............. *C07C 7/04* (2013.01); *C07C 1/20* (2013.01); *C07C 4/18* (2013.01); *C07C 6/126* (2013.01);
(Continued)

(58) Field of Classification Search
CPC .. C07C 15/08; C07C 1/20; C07C 4/18; C07C 6/126; C07C 7/04; C07C 7/08;
(Continued)

(56) References Cited

U.S. PATENT DOCUMENTS 3,931,731 A    1/1976   Fukuda
6,489,528 B2   12/2002  Drake et al.
(Continued)

FOREIGN PATENT DOCUMENTS

CN    1880288 A      12/2006
CN    101820919 A     9/2010
(Continued)

OTHER PUBLICATIONS

The extended European Search Report issued on Apr. 10, 2015, by the European Patent Office in corresponding European Application No. 14191061.2-1454. (5 pages).
(Continued)

*Primary Examiner* — Sharon Pregler
(74) *Attorney, Agent, or Firm* — Buchanan Ingersoll & Rooney PC

(57) ABSTRACT

A method for producing an aromatic hydrocarbon with an oxygenate as raw material, includes: i) reacting an oxygenate in at least one aromatization reactor to obtain an aromatization reaction product; ii) separating the aromatization reaction product to obtain a gas phase hydrocarbons flow X and a liquid phase hydrocarbons flow Y; iii) after removing gas and/or a part of the oxygenate from the gas phase hydrocarbons flow X, a hydrocarbons flow X1 containing a
(Continued)

non-aromatic hydrocarbon is obtained; or after removing gas and/or a part of the oxygenate from the gas phase hydrocarbons flow X, a reaction is conducted in another aromatization reactor and a separation is conducted to obtain a flow X2 containing a non-aromatic hydrocarbon and a flow X3 containing an aromatic hydrocarbon. The flows are further treated.

13 Claims, 9 Drawing Sheets

(51) Int. Cl.
  *C07C 4/18* (2006.01)
  *C07C 7/08* (2006.01)
  *C07C 1/20* (2006.01)
  *C07C 6/12* (2006.01)
(52) U.S. Cl.
  CPC ............ *C07C 7/08* (2013.01); *C07C 2529/18* (2013.01); *C07C 2529/40* (2013.01); *C07C 2529/70* (2013.01)
(58) Field of Classification Search
  CPC ..... C07C 15/04; C07C 15/06; C07C 2529/18; C07C 2529/40; C07C 2529/70
  USPC ....... 585/638, 639, 640, 641, 426, 469, 408, 585/409, 407
  See application file for complete search history.

(56) References Cited

U.S. PATENT DOCUMENTS

| 2010/0185033 A1 | 7/2010 | Karim et al. |
| 2013/0165725 A1 | 6/2013 | Chewter et al. |
| 2016/0102032 A1* | 4/2016 | Du .................. B01J 8/1836 585/323 |

FOREIGN PATENT DOCUMENTS

| CN | 101823929 A | 9/2010 |
| CN | 101671226 B | 4/2012 |
| CN | 101244969 B | 5/2012 |
| CN | 101607864 B | 5/2013 |
| CN | 103406140 A | 11/2013 |
| CN | 103755514 A | 4/2014 |
| CN | 103936541 A | 7/2014 |
| EP | 0090284 A1 | 10/1983 |
| WO | 2015/094698 A1 | 6/2015 |

OTHER PUBLICATIONS

Written Opinion and Search Report issued Dec. 21, 2016, by the Intellectual Property Office of Singapore in Singapore Patent Application No. 10201407097P (8 pages).

Office Action dated Jun. 1, 2017, by the State Intellectual Property Office of People's Republic of China in corresponding Chinese Patent Application No. 201410584706.7. (7 pages).

* cited by examiner

METHOD FOR PRODUCING AN AROMATIC HYDROCARBON WITH AN OXYGENATE AS RAW MATERIAL

TECHNICAL FIELD

The present invention relates to a method for producing an aromatic hydrocarbon with an oxygenate as raw material.

BACKGROUND TECHNOLOGY

Aromatic hydrocarbon (wherein benzene, methylbenzene and dimethylbenzene (i.e. xylene) are referred to be B, T and X respectively and they are jointly called as BTX) is an important basic organic chemical material. Around 90% of aromatic hydrocarbons all over the world comes from the catalytic reforming process of petroleum as raw material and from the gasoline as a byproduct from the steam cracking. Only 10% of the total yield of aromatic hydrocarbons comes from the coal route. With the increasing depletion of petroleum resources and thus the high price thereof, the energy and chemical industry with mainly a petroleum route faces unprecedented serious challenges.

With the development of natural gas and shale gas in North America and Middle East, a large amount of light hydrocarbons are produced as a byproduct. The light hydrocarbon produced by shale gas as byproduct replaces a part of naphtha for steam cracking, and thus a trend of conversion to a light fraction appears in the raw material for steam cracking. In the future, a reduction trend may be seen in the yield of aromatic hydrocarbons from steam cracking byproducts, which results in a shortage trend of the yield of aromatic hydrocarbons all over the world in the future. Thus, the development of a new technology using an oxygenate including methanol as raw material for a partial substitute of the production of aromatic hydrocarbon with petroleum has a great potential.

U.S. Pat. No. 3,931,731 reported a method for the production of gasoline with methanol as raw material. Although a considerable number of aromatic hydrocarbons are present in gasoline, the process takes the production of gasoline liquid fuel with a high octane number as a main target and the product further contains a large amount of isoparaffin components having high octane numbers. Thus, the technology of producing gasoline with oxygenate(s) as raw material(s) has a technical problem of a low total yield of aromatic hydrocarbons.

Chinese patent CN101244969B reported a $C_1$-$C_{12}$ hydrocarbons or a methanol aromatization and catalyst regeneration device. The method does not relate to the conversion of non-hydrocarbons in the reaction product, specific reaction or separation procedures. The added value of non-hydrocarbons in the product is relatively low. Moreover, the production of a large mount of non-hydrocarbons in the product will reduce the efficiency of aromatization of raw material and increase the cost during aromatization.

Chinese patent CN101671226 reported conducting aromatization reaction in an aromatization reactor with a mixture of methanol and one or more of $C_1$-$C_{12}$ hydrocarbons. The method only takes into consideration of a one-time conversion of methanol and $C_1$-$C_{12}$ hydrocarbons and does not relate to a cycle conversion of non-hydrocarbons to aromatic hydrocarbons in the reaction product. Thus, the process has a problem of a low yield of aromatic hydrocarbon. The research shows that the reaction temperature of methane aromatization is up to 700° C., but the conversion rate of methane is less than 20% and the yield of aromatic hydrocarbons is only around 10%. The highest reaction temperature of aromatization in the process is only 650° C. Thus, if the components of $C_1$-$C_{12}$ hydrocarbons contain methane of lower activity, the presence of methane or the accumulation thereof in cycle flow may reduce the utilization efficiency of the reactor.

Chinese patent CN101820919B reported a procedure of producing a dimethylbenzene product with methanol or an oxygenate. In the procedure, B and T in the liquid phase aromatic hydrocarbon product are separated one by one, as well as non-aromatic hydrocarbons having more than 6 carbon numbers are also separated. In the aromatic hydrocarbon mixture, non-aromatic hydrocarbons and aromatic hydrocarbons with the same number of carbon atoms have extremely close boiling points and it is very difficult to separate them. The current technique of separating aromatic hydrocarbon usually achieves the separation of non-aromatic hydrocarbons from aromatic hydrocarbons by a manner of solvent extraction of a mixed hydrocarbons flow containing benzene, methylbenzene and dimethylbenzene light aromatic hydrocarbon and then separates benzene, methylbenzene, dimethylbenzene and $C_9^+$ aromatic hydrocarbon one by one. In the procedure disclosed in Chinese patent CN101820919B, non-aromatic hydrocarbons having no more than 6 carbon numbers are subjected to a cycle conversion to aromatic hydrocarbon. However, non-aromatic hydrocarbons having more than 6 carbon numbers are not subjected to a cycle conversion to aromatic hydrocarbon. Thus, a problem of a low aromatic hydrocarbon yield is present during the process. As compared to the direction utilization of a hydrocarbons mixture containing B and T, the energy consumption during the separation process of liquid phase aromatic hydrocarbon from non-aromatic hydrocarbon in Chinese patent CN101820919B will be higher. Moreover, in said procedure, simply only $H_2$ and $CH_4$ are removed from the gas phase components thereof. Oxygenates such as CO, $CO_2$, formaldehyde, formic acid and acetic acid are produced inevitably during the process of producing aromatic hydrocarbon with oxygenates. These components cannot be further converted to aromatic hydrocarbon. Without removal, they will be accumulated in the reaction system and thus affect the efficiency of the reactor.

Chinese patent CN101607864B reported a method of increasing the yield of dimethylbenzene by adding benzene or methylbenzene to the aromatization system of oxygenate. In the product of producing aromatic hydrocarbon with oxygenate, there are a large amount of non-aromatic hydrocarbons, unconverted oxygenates and intermediate product of oxygenate in addition to aromatic hydrocarbon products. Theses non-aromatic hydrocarbon products have a large amount of components. If Separating them or selling them as mixture, their added values are relatively low. By adding benzene or methylbenzene components from the reaction products or from outside to the aromatization process, the yield of dimethylbenzene product may be increased via the alkylation of methanol. However, the method requires relatively high energy consumption for separating benzene and methylbenzene respectively, which will necessarily increase the production cost of aromatic hydrocarbon. In addition, the aromatization catalyst used in the method uses a molecular sieve catalyst upon silanization and metal modification. Although the silanization modification will improve the shape selectivity of the catalyst to a certain degree, it will cause the blockage of pores and reduction of catalyst activity.

Chinese patent application CN1880288A reported a process of methanol conversion for preparing aromatic hydrocarbons and catalyst. In the technique of preparing aromatic hydrocarbons with methanol disclosed by the above patent, two fixed-bed reactors in series are used; after the reactant, methanol, enters the first section of the reactor for reaction, the first section of the gas phase product continues to enter the second section of reactor for reaction, aromatic hydrocarbon and non-aromatic hydrocarbon are obtained upon separation of the first and second sections of liquid phase products. The process of producing aromatic hydrocarbons with oxygenates is a process of strong exothermicity and relatively rapid deactivation due to carbon deposition. The fixed-bed reactor has a difficulty of heat transfer and heat removal and has a problem of being difficult to control the temperature stably. In the process, only the gas phase components in the byproducts of the first reactor are used for aromatization thereof for conversation to aromatic hydrocarbons. The non-aromatic hydrocarbons as the byproducts in the second reactor are not further subjected to cycle conversion to aromatic hydrocarbon. Thus, the process has a technical problem of a low total yield of aromatic hydrocarbon.

U.S. patent application US20100185033A1, reported a method of producing aromatic hydrocarbons with aliphatic alcohols having carbon numbers between 1 and 10 as raw material. The catalyst is a molecular sieve catalyst loaded with 0.0001 to 20% of La and 0.0001-20% of M metal, wherein M is selected from at leas one of molybdenum (Mo), cerium (Ce), or caesium (Cs) and the zeolite is selected from ZSM-5, ZSM-11, ZSM-23, ZSM-48 and ZSM-57. The reaction process conditions are a temperature of 250 to 750° C., a pressure of 0 to 3 MPa, a raw material space velocity of 0.1 to 500 h$^{-1}$. The method does not relate to a step of producing aromatic hydrocarbon by a further cycle conversion of a byproduct, non-aromatic hydrocarbons. Thus, the process has a problem of a low total yield of aromatic hydrocarbons.

U.S. Pat. No. 6,489,528B2 reported a method of producing aromatic hydrocarbon with methanol or dimethyl ether as raw material and two types of molecular sieve catalysts, wherein one of them is a silicoaluminophosphate molecular sieve and another one is a ZSM-5 molecular sieve catalyst which contains a metal Zn and an element from Group IIIA or Group VIB. The method does not mention specific reaction and separation procedures and there is no further utilization solution of non-aromatic hydrocarbon components in the product.

In addition to aromatic hydrocarbon products, there are a large amount of non-aromatic hydrocarbon hydrocarbons components, a small amount of unconverted oxygenate materials and other intermediate oxygenate components as byproducts in the products from the production of aromatic hydrocarbons with oxygenates. These components are very complicated. The economy of using them alone upon separation is poor. As fuel gas, their added values are also very low. If such part of components can be converted to aromatic hydrocarbons, a total yield of aromatic hydrocarbons in the production of aromatic hydrocarbons with oxygenates can be notably improved, the production cost of aromatic hydrocarbons can be reduced and a notable economic benefit is produced.

In the components of aromatic hydrocarbons, a light aromatic hydrocarbon—BTX is an aromatic hydrocarbon product having the most wide value and use. In the aromatic hydrocarbon components, dimethylbenzene is a product having a relatively wide use and a relatively high added value. In the aromatic hydrocarbon products, the paths for using methylbenzene directly are very limited. Its main use is converting methylbenzene to dimethylbenzene product which is in great demand and has a relatively high added value through selective disproportionation of methylbenzene or a transalkylation process with a $C_9$ component.

Introducing non-metal oxides and metal oxides, especially non-metal oxides, for modification is reported in the prior art. However, the presence of these components may cause a blockage of molecular sieve pores, a failure to achieve the optimum modification effect and a reduction of aromatization yield of catalyst.

To sum up, the technical problem of a low total yield of aromatic hydrocarbons and a high energy consumption si present during the process of producing aromatic hydrocarbons with oxygenates as raw material in the prior art.

THE CONTENTS OF THE INVENTION

The technical problem to be solved by the present invention is providing a method for producing an aromatic hydrocarbon with an oxygenate as raw material. The method has advantages of a high yield of an aromatic hydrocarbon and a low energy consumption.

The present invention relates to a method for producing an aromatic hydrocarbon with an oxygenate as raw material, comprising
i) reacting an oxygenate in at least one aromatization reactor to obtain an aromatization reaction product;
ii) separating the aromatization reaction product through a separation unit A to obtain a gas phase hydrocarbons flow X and a liquid phase hydrocarbons flow Y;
iii) after removing gas and/or a part of the oxygenate from the gas phase hydrocarbons flow X through a separation unit B, a hydrocarbons flow X1 containing a non-aromatic hydrocarbon is obtained; or after removing gas and/or a part of the oxygenate from the gas phase hydrocarbons flow X through a separation unit B, a reaction is conducted in another aromatization reactor and a separation is conducted through a separation unit A to obtain a flow X2 containing a non-aromatic hydrocarbon and a flow X3 containing an aromatic hydrocarbon;
iv) after combining the liquid phase hydrocarbons flow Y and optionally the flow X3 containing an aromatic hydrocarbon, a mixed hydrocarbons flow M of an aromatic hydrocarbon having less than or equal to 7 carbon numbers and a flow N of the residual hydrocarbons is obtained by a non-precise rectification of a separation unit C;
v) separating the flow N of the residual hydrocarbons through a separation unit D to obtain a flow K containing a non-aromatic hydrocarbon, a $C_8$ aromatic hydrocarbon flow J and a $C_9^+$ aromatic hydrocarbon flow L;
vi) returning one of the hydrocarbons flow X1 containing a non-aromatic hydrocarbon and the flow X2 containing a non-aromatic hydrocarbon, the mixed hydrocarbons flow M of an aromatic hydrocarbon having less than or equal to 7 carbon numbers and/or a part or all of the flow K containing a non-aromatic hydrocarbon, optionally with an additional $C_2^+$ hydrocarbons flow, to the above oxygenate; or returning one of the hydrocarbons flow X1 containing a non-aromatic hydrocarbon and the flow X2 containing a non-aromatic hydrocarbon, a mixed hydrocarbons flow M of an aromatic hydrocarbon having less than or equal to 7 carbon numbers and/or a part or all of the flow K containing a non-aromatic hydrocarbon to the aromatization reactor in iii);
vii) optionally, reacting the $C_9^+$ aromatic hydrocarbons flow L in at least one reactor selected from a transalkylation reactor and a dealkylation reactor to obtain a $C_8$ aromatic hydrocarbon flow L1.

Therein the oxygenate is preferably selected from at least one of methanol and dimethyl ether. The separation unit A preferably comprises operation units such as quenching, alkaline washing and/or water washing and the like. The separation unit B preferably comprises at least one of separation manners such as pressure swing adsorption, rectification and adsorption. The separation unit C is a non-precise rectification separation unit, by which a liquid phase hydrocarbons flow Y containing a non-aromatic hydrocarbon and an aromatic hydrocarbon can be separated to a mixed hydrocarbons flow M of an aromatic hydrocarbon having less than or equal to 7 carbon numbers and a mixed hydrocarbons flow N of the residual hydrocarbons and non-aromatic hydrocarbons. This is different from the precise rectification separation of aromatic hydrocarbon in the prior art. The precise rectification separation of an aromatic hydrocarbon in the prior art can separate non-hydrocarbon components of the flow Y from aromatic hydrocarbon components completely by solvent extraction and further separate the aromatic hydrocarbon mixture thereof to benzene, methylbenzene, $C_8$ aromatic hydrocarbon and $C_9^+$ aromatic hydrocarbon. The separation unit D preferably comprises at least one of rectification and solvent extraction rectification.

In the above method of the present invention, the liquid phase hydrocarbons flow Y is preferably separated according to the following two separation manners:

1) flow Y enters a separation unit C1 and is separated by a non-precise rectification to obtain a mixed hydrocarbons flow M1 of aromatic hydrocarbons having less than or equal to 6 carbon numbers and a hydrocarbons flow N1 having more than 6 carbon numbers, and the hydrocarbons flow N1 enters a separation unit D1 to be able to obtain a $C_8$ aromatic hydrocarbon flow and a $C_9^+$ aromatic hydrocarbon flow, for example, with reference to FIG. 9, the separation flow chart;

2) flow Y enters a separation unit C2 and is separated by a non-precise rectification to obtain a mixed hydrocarbons flow M2 of aromatic hydrocarbons having less than or equal to 7 carbon numbers and a hydrocarbons flow N2 having more than 7 carbon numbers, and the hydrocarbons flow N2 enters a separation unit D2 to be able to obtain a $C_8$ aromatic hydrocarbon flow and a $C_9^+$ aromatic hydrocarbon flow, with reference to FIG. 10, the separation flow chart.

In the method of the present invention, a part or all of the flow containing non-aromatic hydrocarbons and the flow of the oxygenate may come into contact with a catalyst for reaction in the same aromatization reactor or by entering different aromatization reactors respectively. The method of the present invention preferably comprises at least one reactor selected from the group consisting of a transalkylation reactor and a dealkylation reactor for converting a $C_9^+$ aromatic hydrocarbon flow L in the product of aromatic hydrocarbon to dimethylbenzene; the reaction conditions for said transalkylation reactor are preferably a temperature of 350 to 550° C., a reaction pressure of 0.1 to 5.0 MPa, a molar ratio of hydrogen/hydrocarbon of 1:1 to 200:1, a weight space velocity of raw material(s) of 0.1 to 15 $h^{-1}$; the reaction conditions of said dealkylation reactor are: a reaction temperature of 300 to 800° C., a molar ratio of hydrogen/hydrocarbon of 0.1 to 200:1 and a weight space velocity of the hydrocarbons of 0.5 to 10 $h^{-1}$.

When the method of the present invention contains one aromatization reactor, the method of the present invention is conducted according to the following steps:

a) under the process conditions of a temperature of 400 to 550° C., a pressure of 0.01 to 2.0 MPa and a weight space velocity of raw material(s) of 0.1 to 4 $h^{-1}$, contacting a flow 1 of oxygenate(s) with a catalyst for reaction in an aromatization reactor to obtain a hydrocarbons flow 3;

b) removing $CO_2$ and a part of oxygenate(s) from said hydrocarbons flow 3 through a separation unit 1 to obtain a gas phase non-aromatic hydrocarbons flow 4, a liquid phase hydrocarbons flow 5 containing an aromatic hydrocarbon and an aqueous phase;

c) removing gas, such as, inorganic gas comprising $H_2$, CO, $CO_2$, $N_2$ and the like, $CH_4$ and a part of oxygenate(s) from said gas phase non-aromatic hydrocarbons flow 4 through a separation unit 2 to obtain a $C_2^+$ hydrocarbons flow 6;

d) further separating the liquid phase hydrocarbons flow 5 containing an aromatic hydrocarbon according to one of the following four manners, and reacting:

d1) for example, with reference to FIG. 1, subjecting the liquid phase hydrocarbons flow 5 containing an aromatic hydrocarbon to non-precise rectification through a separation unit 3 to obtain a hydrocarbon flow 7 of aromatic hydrocarbons having less than or equal to 7 carbon numbers and a hydrocarbon flow 8 of aromatic hydrocarbons having more than 7 carbon numbers, and separating said hydrocarbons flow 8 through a separation unit 4 to obtain a hydrocarbons flow 9, a flow 10 containing $C_8$ aromatic hydrocarbon and a $C_9^+$ aromatic hydrocarbon flow 11, and reacting said flow 11 in a dealkylation reactor to obtain a $C_8$ aromatic hydrocarbon flow 201;

obtaining a hydrocarbons flow 2 of aromatic hydrocarbons having less than or equal to 7 carbon numbers from the hydrocarbons flow 7 and a part or all of the $C_2^+$ hydrocarbons flow 6, wherein said hydrocarbons flow 2 further optionally comprises a part or all of at least one selected from the hydrocarbons flow 9 and a $C_2^+$ hydrocarbons flow 101 outside the reaction-separation system; and returning said hydrocarbons flow 2 to the oxygenate(s) flow 1 for further reaction;

d2) for example, with reference to FIG. 2, subjecting the liquid phase hydrocarbons flow 5 containing an aromatic hydrocarbon to a non-precise rectification through a separation unit 3 to obtain a hydrocarbon flow 7 of aromatic hydrocarbons having less than or equal to 7 carbon numbers and a hydrocarbon flow 8 of aromatic hydrocarbons having more than 7 carbon numbers, and obtaining a hydrocarbons flow 9 containing non-aromatic hydrocarbons, a flow 10 containing $C_8$ aromatic hydrocarbons and a $C_9^+$ aromatic hydrocarbon flow 11 from said hydrocarbons flow 8 through a separation unit 4;

obtaining a hydrocarbon flow 15 containing dimethylbenzene from a $C_9^+$ aromatic hydrocarbon flow 12 and a methylbenzene flow 13 outside the reaction-separation system through a transalkylation reactor, wherein the $C_9^+$ aromatic hydrocarbon flow 12 is selected from one of a part or all of a $C_9^+$ aromatic hydrocarbon flow 11 or a mixture of a part or all of the $C_9^+$ aromatic hydrocarbon flow 11 and a $C_9^+$ aromatic hydrocarbon flow 106 outside the reaction-separation system;

obtaining a hydrocarbons flow 2 of aromatic hydrocarbon having less than or equal to 7 carbon numbers from the hydrocarbons flow 7 and a part or all of a $C_2^+$ hydrocarbons flow 6, wherein said hydrocarbons flow 2 further optionally comprises a part or all of at least one selected from the hydrocarbons flow 9 and a $C_2^+$ hydrocarbons flow 101 outside the reaction-separation system; and returning said hydrocarbons flow 2 to the oxygenate(s) flow 1 for further reaction;

d3) for example, with reference to FIG. 3, subjecting the liquid phase hydrocarbons flow 5 containing an aromatic hydrocarbon to a non-precise rectification through a separation unit 5 to obtain a hydrocarbon flow 21 of aromatic hydrocarbon having less than or equal to 6 carbon numbers and a hydrocarbons flow 22 of aromatic hydrocarbon having more than 6 carbon numbers, and obtaining a hydrocarbons flow 23 containing non-aromatic hydrocarbons, a methylbenzene flow 24, a flow 25 containing $C_8$ aromatic hydrocarbons and a $C_9^+$ aromatic hydrocarbon flow 26 from said flow 22 through a separation unit 6;

obtaining a hydrocarbons flow 2 of aromatic hydrocarbons having less than or equal to 7 carbon numbers from a part or all of the hydrocarbons flow 6 and the hydrocarbons flow 21, wherein said hydrocarbons flow 2 further optionally comprises a part or all of at least one selected from the hydrocarbons flow 23 and a $C_2^+$ hydrocarbons flow 101 outside the reaction-separation system; and returning said hydrocarbons flow 2 to the oxygenate flow 1 for further reaction;

d4) for example, with reference to FIG. 4, subjecting the liquid phase hydrocarbons flow 5 containing an aromatic hydrocarbon to a non-precise rectification through a separation unit 5 to obtain a hydrocarbons flow 21 of aromatic hydrocarbons having less than or equal to 6 carbon numbers and a hydrocarbons flow 22 of aromatic hydrocarbons having more than 6 carbon numbers, and obtaining a hydrocarbon flow 23 containing non-aromatic hydrocarbons, a methylbenzene flow 24, a flow 25 containing $C_8$ aromatic hydrocarbons and a $C_9^+$ aromatic hydrocarbon flow 26 from said flow 22 through a separation unit 6;

contacting a methylbenzene flow 27 and a $C_9^+$ aromatic hydrocarbon flow 28 with a catalyst in a transalkylation reactor to obtain a flow 29 containing dimethylbenzene, wherein said flow 27 is selected from one of a part or all of the methylbenzene flow 24 or a mixed flow of a part or all of the flow 24 and a methylbenzene flow 105 outside the reaction-separation system, and said $C_9^+$ aromatic hydrocarbon flow 28 is selected from one of a part or all of the flow 26 or a mixed flow of a part or all of the flow 26 and a $C_9^+$ aromatic hydrocarbon flow 106 outside the reaction-separation system;

obtaining a hydrocarbons flow 2 of aromatic hydrocarbons having less than or equal to 7 carbon numbers from a part or all of the hydrocarbon flow 6 and the hydrocarbons flow 21, wherein said hydrocarbons flow 2 further optionally comprises a part or all of at least one selected from the flow 23 and a $C_2^+$ hydrocarbons flow 101 outside the reaction-separation system; and returning said hydrocarbons flow 2 to the oxygenate(s) flow 1 for further reaction.

When the method of the present invention contains two aromatization reactors, the method of the present invention is conducted according to the following steps.

h) under the process conditions of a temperature of 400 to 550° C., a reaction pressure of 0.01 to 2.0 MPa and a weight space velocity of raw material(s) of 0.1 to 4 $h^{-1}$, contacting a flow 1 of oxygenate(s) with a catalyst for reaction in a first aromatization reactor to obtain a hydrocarbons flow 3;

i) removing $CO_2$ and a part of acidic oxygenate to obtain a gas phase non-aromatic hydrocarbon flow 4, a liquid phase hydrocarbons flow 5 containing aromatic hydrocarbons and an aqueous phase from a flow 3 through a separation unit 1;

j) removing gas, such as, inorganic gas comprising $H_2$, CO, $CO_2$, $N_2$ and the like, $CH_4$ and a part of oxygenate(s) from said hydrocarbons flow 31 through a separation unit 2 to obtain a $C_2^+$ non-aromatic hydrocarbons flow 32, wherein the hydrocarbons flow 31 is a mixed hydrocarbons flow of the flow 4 and the flow 35;

k) under the process conditions of a temperature of 450 to 650° C., a reaction pressure of 0.01 to 2.0 MPa and a weight space velocity of raw material(s) of 0.1 to 4 $h^{-1}$, contacting a hydrocarbons flow 33 with a catalyst in a second aromatization reactor to obtain a hydrocarbons flow 34, wherein said hydrocarbons flow 33 is selected from a mixed hydrocarbons flow of the flow 32 and a flow I, wherein the flow I is selected from a part or all of at least one of a $C_2^+$ non-aromatic hydrocarbon flow 102 outside the reaction-separation system and a flow 39;

l) removing $CO_2$ and a part of acidic oxygenate to obtain a gas phase non-aromatic hydrocarbon flow 35, a liquid phase hydrocarbons flow 36 containing aromatic hydrocarbons and an aqueous phase from the hydrocarbons flow 34 through a separation unit 7;

m) further separating the flow 5 and the flow 36 according to one of the following four manners, and reacting:

m1) for example, with reference to FIG. 5, separating the flow 5 and the flow 36 in a separation unit 8 by a non-precise rectification to obtain a hydrocarbons flow 37 of aromatic hydrocarbons having less than or equal to 7 carbon numbers and a hydrocarbons flow 38 of aromatic hydrocarbons having more than 7 carbon numbers, and separating said flow 38 through a separation unit 9 to obtain the flow 39 containing non-aromatic hydrocarbons, a $C_8$ aromatic hydrocarbon flow 40 and a $C_9^+$ aromatic hydrocarbon flow 41, and reacting said $C_9^+$ aromatic hydrocarbon flow 41 or a mixed hydrocarbons flow of the $C_9^+$ aromatic hydrocarbon flow 41 and optionally a $C_9^+$ aromatic hydrocarbon flow 106 in a dealkylation reactor to obtain a $C_8$ aromatic hydrocarbon flow 202;

obtaining a hydrocarbons flow 2 of aromatic hydrocarbons having less than or equal to 7 carbon numbers from the hydrocarbons flow 37 and a flow H, wherein said flow H is selected from at least one of a $C_2^+$ hydrocarbons flow 101 outside the reaction-separation system and the flow 39; and returning said hydrocarbons flow 2 to the oxygenate(s) flow 1 for further reaction;

m2) for example, with reference to FIG. 6, separating the flow 5 and the flow 36 in a separation unit 8 by a non-precise rectification to obtain a hydrocarbons flow 37 of aromatic hydrocarbons having less than or equal to 7 carbon numbers and a hydrocarbons flow 38 having more than 7 carbon numbers, and separating said flow 38 through a separation unit 9 to obtain the flow 39 containing non-aromatic hydrocarbons, a $C_{8-}$ aromatic hydrocarbon flow 40 and a $C_9^+$ aromatic hydrocarbon flow 41, obtaining a flow 44 containing $C_8$ aromatic hydrocarbons from a $C_9^+$ aromatic hydrocarbon flow 42 and a methylbenzene flow 43 outside a reaction-separation system, wherein the $C_9^+$ aromatic hydrocarbon flow 42 is selected from the flow 41 or a mixed flow of the flow 41 and a $C_9^+$ aromatic hydrocarbon flow 106 outside the reaction-separation system, obtaining a hydrocarbons flow 2 of aromatic hydrocarbons having less than or equal to 7 carbon numbers from the hydrocarbons flow 37 and a flow H, wherein said flow H is selected from at least one of a $C_2^+$ hydrocarbons flow 101 outside the reaction-separation system and the flow 39; and returning said hydrocarbons flow 2 to the oxygenate(s) flow 1 for further reaction;

m3) for example, with reference to FIG. 7, separating the flow 5 and the flow 36 in a separation unit 10 by a non-precise rectification to obtain a hydrocarbons flow 47 of aromatic hydrocarbons having less than or equal to 7 carbon numbers and a hydrocarbons flow 48 having more than 7 carbon numbers, and separating said flow 48 through a separation unit 11 to obtain the flow 49 containing non-aromatic hydrocarbons, a $C_{8-}$ aromatic hydrocarbon flow 50 and a $C_9^+$ aromatic hydrocarbon flow 51;

obtaining a hydrocarbons flow 2 of aromatic hydrocarbons having less than or equal to 7 carbon numbers from the flow 47 and a flow H, wherein said flow H is selected from at least one of $C_2^+$ hydrocarbons flow 101 outside the reaction-separation system and the flow 49; and returning said hydrocarbons flow 2 to the oxygenate flow 1 for further reaction;

m4) for example, with reference to FIG. 8, separating the flow 5 and the flow 36 in a separation unit 9 by a non-precise rectification to obtain a hydrocarbons flow 47 of aromatic hydrocarbons having less than or equal to 7 carbon numbers and a hydrocarbons flow 48 having more than 7 carbon numbers, and separating said flow 48 through a separation unit 9 to obtain a flow 49 containing non-aromatic hydrocarbons, a $C_8$ aromatic hydrocarbon flow 50 and a $C_9^+$ aromatic hydrocarbon flow 51, obtaining a flow 54 containing $C_8$ aromatic hydrocarbons from a $C_9^+$ aromatic hydrocarbon flow 52 and a methylbenzene flow 53 outside the reaction-separation system, wherein the $C_9^+$ aromatic hydrocarbon flow 52 is selected from the flow 51 or a mixed flow of the flow 51 and a $C_9^+$ aromatic hydrocarbon flow 106 outside the reaction-separation system, obtaining a hydrocarbons flow 2 of aromatic hydrocarbons having less than or equal to 7 carbon numbers from the flow 47 and a flow H, wherein said flow H is selected from at least one of $C_2^+$ hydrocarbon flow 101 outside the reaction-separation system or the flow 49; and returning said hydrocarbons flow 2 to the oxygenate flow 1 for further reaction.

The aromatization reactor used in the aromatization reaction may be at least one of a fluidized-bed reactor, a fixed-bed reactor and a moving-bed reactor. The aromatization reactor preferably is a fluidized-bed reactor and a moving-bed reactor, optionally with different regeneration systems or with a common regeneration system. The transalkylation reactor may be a fixed-bed reactor.

The aromatization catalyst comprise at least one molecular sieve active component selected from ZSM-11 and ZSM-5 molecular sieves, and the molar ratio of silicon oxide to aluminium oxide in the molecular sieve is 10:1 to 200:1. The transalkylation catalyst comprises at least one molecular sieve active component selected from MOR, ZSM-5 and BETA molecular sieves. The dealkylation process may be free of catalyst or has a catalyst selected from oxide and molecular sieve type dealkylation catalysts. The molecular sieve component prior to the molding of the aromatization catalyst or the catalyst supporting the modification component is preferably subjected to a high temperature hydrothermal treatment, wherein the conditions of the hydrothermal treatment are preferably a temperature of 400 to 750° C., a partial pressure of water vapor of 5 to 100%, a treatment time period of 0.5 to 96 hours.

Molding manners such as band extrusion or tablet compressing are used in the fixed-bed catalyst. A molding manner of ball rolling may be used in the moving-bed catalyst. The fixed-bed catalyst and the moving-bed catalyst may contain a certain amount of adhesive components, such as amorphous silicon oxide, aluminium oxide or zirconium oxide and the like. In order to enhance the aromatization property of the fluidized-bed catalyst, for example the conversion capability of an oxygenate, the total yield of aromatic hydrocarbon, the selectivity of aromatic hydrocarbon and the hydrothermal stability of the catalyst, metal oxide or non-metal oxide for modification of catalyst may be introduced prior to or after molding of catalyst. Preferably a precursor component having a relatively good water solubility is used.

The fluidized-bed catalyst is produced by a spraying molding drying method. The fluidized-bed catalyst contains clay components for enhancing the strength and the antiwear property of fluidized-bed catalyst, such as kaolin, montmorillonite and hargil and the like. In addition, the components of the fluidized-bed catalyst further contain active components for adhering catalysts—molecular sieve and clay components, such as amorphous silicon oxide, aluminium oxide or zirconium oxide and the like. In order to enhance the aromatization property of the fluidized-bed catalyst, such as the conversion capability of an oxygenate, the total yield of aromatic hydrocarbon, the selectivity of aromatic hydrocarbon and the hydrothermal stability of the catalyst, metal oxide or non-metal oxide for modification may be introduced to the composition of the catalyst.

In the products of the present invention, a mixed hydrocarbons flow of aromatic hydrocarbons having less than or equal to 7 carbon numbers enters the same aromatization reactor with an oxygenate. In the said aromatization reactor, in addition to the conversion of the oxygenate to an aromatic hydrocarbon, at least one of benzene or methylbenzene in the mixed hydrocarbons of aromatic hydrocarbons having less than or equal to 7 carbon numbers of the product can be converted to a dimethylbenzene product through alkylation reaction with the oxygenate, and thereby the added value of the aromatic hydrocarbon product is improved. Meanwhile, the non-aromatic hydrocarbon components in the mixed hydrocarbon flow of aromatic hydrocarbons having less than or equal to 7 carbon numbers of the product can be subjected to an aromatization reaction simultaneously and thus produce aromatic hydrocarbon to improve the total yield of aromatic hydrocarbon. In the reaction products, except a hydrocarbons flow M containing aromatic hydrocarbons having less than or equal to 7 carbon numbers, the non-aromatic hydrocarbon hydrocarbons components may enter at least one aromatization reactor for a cycle conversion to aromatic hydrocarbon so as to improve the yield of aromatic hydrocarbon during the process.

The aromatic hydrocarbon separation technique in the prior art separates the liquid phase product containing aromatic hydrocarbons having more than 5 carbon numbers by solvent extraction and rectification unit operation to obtain non-aromatic hydrocarbon components, benzene, methylbenzene, $C_8$ aromatic hydrocarbon and a heavy aromatic hydrocarbon having more than 9 carbon numbers one by one by a manner of precise separation. By doing so, both the energy consumption and material consumption during the separation process are relatively large, which will undoubtedly increase the cost of the production of aromatic hydrocarbon from the oxygenate greatly. As compared to the reaction-separation technique of aromatic hydrocarbon in the prior art, the solution used in the present invention firstly separates the liquid phase product containing aromatic hydrocarbons having more than 5 carbon numbers into a hydrocarbons flow of aromatic hydrocarbon having less than or equal to 7 carbon numbers and a hydrocarbons flow containing $C_8$ aromatic hydrocarbon by a non-precise separation manner. The hydrocarbons flow of aromatic hydrocarbon having less than or equal to 7 carbon numbers can enter the same aromatization reactor with the oxygenate without further separation. The benzene or methylbenzene component in the hydrocarbons flow of aromatic hydrocarbons having less than or equal to 7 carbon numbers can be subjected to an alkylation reaction with the oxygenate for a cycle conversion to dimethylbenzene. Meanwhile, the non-aromatic hydrocarbon hydrocarbons component in the hydrocarbons flow containing $C_8$ aromatic hydrocarbon may enter one or more aromatization reactor(s) for a cycle conversion to aromatic hydrocarbon to further improve the total yield of aromatic hydrocarbon. As compared to the prior art, using the reaction-separation solution provided in the present invention can partially or wholly omit the step of separating non-aromatic hydrocarbons from aromatic hydrocarbons and BTX aromatic hydrocarbons one by one and save a large amount of material consumption and energy consumption in separation and thus reduce the production cost during the process.

In the solution provided in the present invention, the removal of non-aromatized active $H_2$, CO, $CO_2$ and a part of acidic oxygenates from the gas phase non-aromatic hydrocarbon components through separation operation, followed by a cycle conversion in an aromatization reactor, prevents the accumulation of the above substances in reaction materials, improves the efficiency of the reactor and can effectively reduce a corrosion of acidic oxygenates on devices and pipelines. The present invention also provides a solution of incorporating transalkylation or dealkylation reactors. The $C_9^+$ heavy aromatic hydrocarbons in the product are converted to dimethylbenzene by reacting with the methylbenzene in the product or outside the reaction-separation system in a dealkylation reactor, or the $C_9^+$ heavy aromatic hydrocarbons in the product is converted to $C_8$ aromatic hydrocarbon, such as dimethylbenzene, through dealkylation reaction in a dealkylation reactor, which improves the yield of $C_8$ aromatic hydrocarbons and facilitates the improvement of the added value of the product.

To sum up, as compared to the prior art, the present invention comprises at least one aromatization reactor. A hydrocarbons mixture of aromatic hydrocarbons having less than or equal to 7 carbon numbers enters the same reactor directly with the oxygenate as raw material for reaction without complete precise separation. The residual non-aromatic hydrocarbon hydrocarbons may enter one or more aromatization reactor(s) within the reaction-separation system. It can not only realize the aromatization of the oxygenate but also convert the non-aromatic hydrocarbons containing byproducts to aromatic hydrocarbon, and convert a hydrocarbons flow containing benzene and methylbenzene in the reaction product to aromatic hydrocarbon or a dimethylbenzene product having a high added value, which improves the total yield of aromatic hydrocarbon and the yield of dimethylbenzene of the above process. In addition, as compared to the prior art, in the solution provided in the present invention, the hydrocarbons mixture of aromatic hydrocarbons having less than or equal to 7 carbon numbers enters the same reactor directly with the oxygenate as raw material for reaction without precise separation, which greatly saves the energy consumption and the material consumption in separation.

THE DESCRIPTION OF FIGURES

SPECIFIC EMBODIMENTS

The present invention is further elaborated with the following specific Examples.

Example 1

Figure 1:
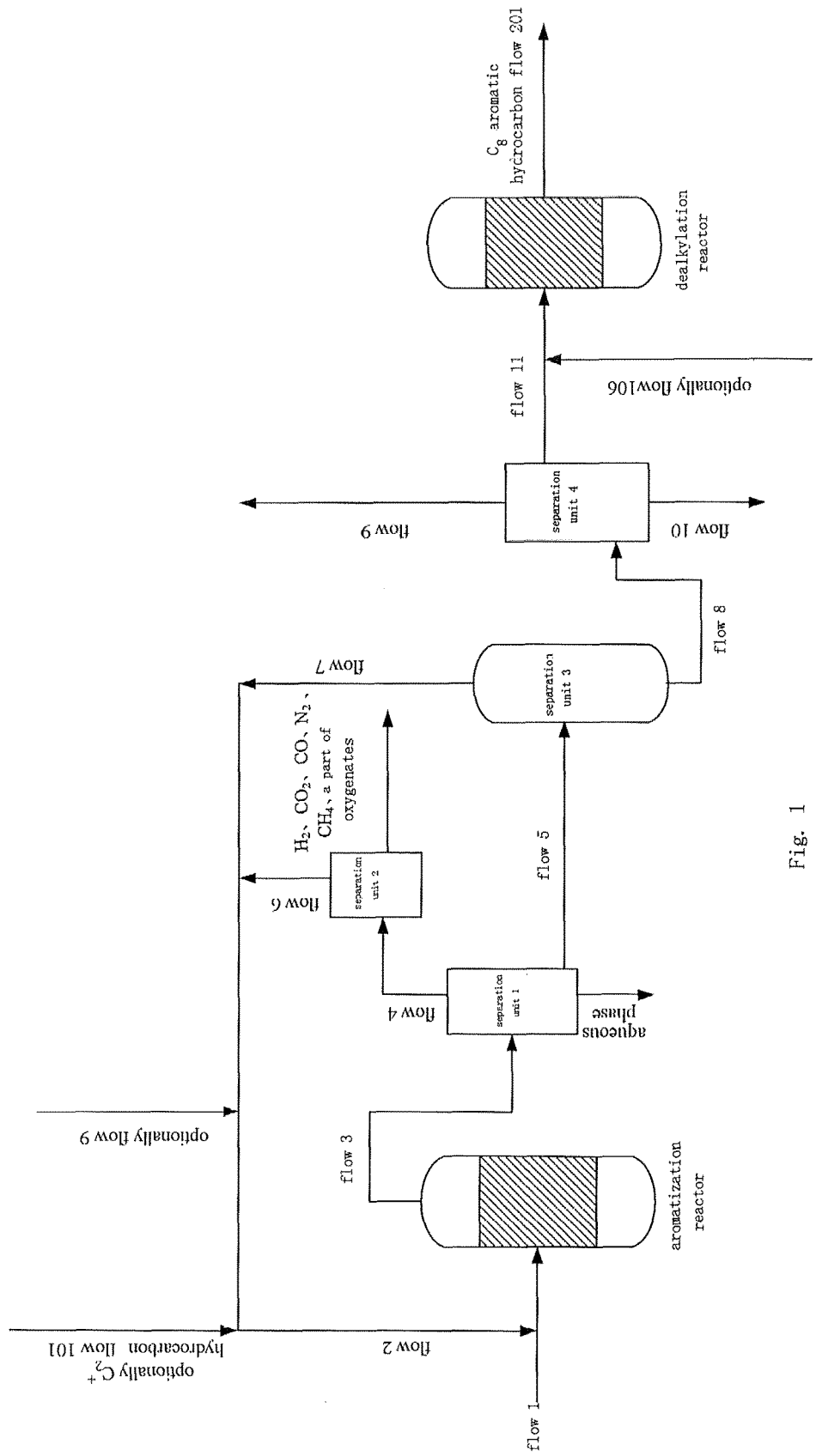
FIG. 1 is a flow chart of one embodiment of the present invention.

With reference to the reaction-separation flow chart of, for example, FIG. 1, it had the following steps:
a) contacting the methanol flow 1 in an aromatization reactor with a catalyst for reaction under the process conditions of a temperature of 400° C., a pressure of 0.05 MPa, a methanol weight space velocity of 0.1 $h^{-1}$ to obtain the hydrocarbons flow 3;
b) removing $CO_2$ and a part of oxygenates from the flow 3 through the separation unit 1 to obtain the gas phase non-aromatic hydrocarbons flow 4, the liquid hydrocarbons flow 5 containing aromatic hydrocarbons and the aqueous phase;
c) removing inorganic gases such as $H_2$, CO, $CO_2$, $N_2$ and the like, $CH_4$ and a part of oxygenates from the flow 4 through the separation unit 2 via pressure swing adsorption to obtain a $C_2^+$ hydrocarbons flow 6;
d) subjecting the hydrocarbons flow 5 to a non-precise rectification through the separation unit 3 to obtain the hydrocarbons flow 7 of aromatic hydrocarbons having less than or equal to 7 carbon numbers and a hydrocarbons flow 8 of aromatic hydrocarbons having more than 7 carbon numbers, and obtaining the hydrocarbons flow 9, the flow 10 containing $C_8$ aromatic hydrocarbon and the $C_9^+$ aromatic hydrocarbon flow 11 from the hydrocarbons flow 8 through the separation unit 4;
e) returning the above hydrocarbons flow 2 of aromatic hydrocarbons having less than or equal to 7 carbon numbers consisting of the $C_2^+$ hydrocarbons flow 6, the hydrocarbons flow 7 and the hydrocarbons flow 9 to the above methanol flow 1 for further reaction;
f) reacting the $C_9^+$ aromatic hydrocarbon flow 11 in a dealkylation reactor under the conditions of 750° C., a hydrocarbons weight space velocity of 8 $h^{-1}$ and a reaction pressure of 5 MPa to obtain a $C_8$ aromatic hydrocarbon flow 201, without any catalyst during this reaction process.

The aromatization reactor was of a fixed-bed form. The catalyst contained ZSM-5 molecular sieve active components having silicon oxide and aluminium oxide in a molar ratio of 10:1, wherein the catalyst was treated for 0.5 hour at 750° C. and a water vapor partial pressure of 100% before use.

In the present Example, the conversion rate of methanol was more than 99%; the yield of dimethylbenzene was 81.5% and the total yield of aromatic hydrocarbon was 84.8%, based on the weight of carbon and hydrogen of methanol.

Example 2

Figure 2:
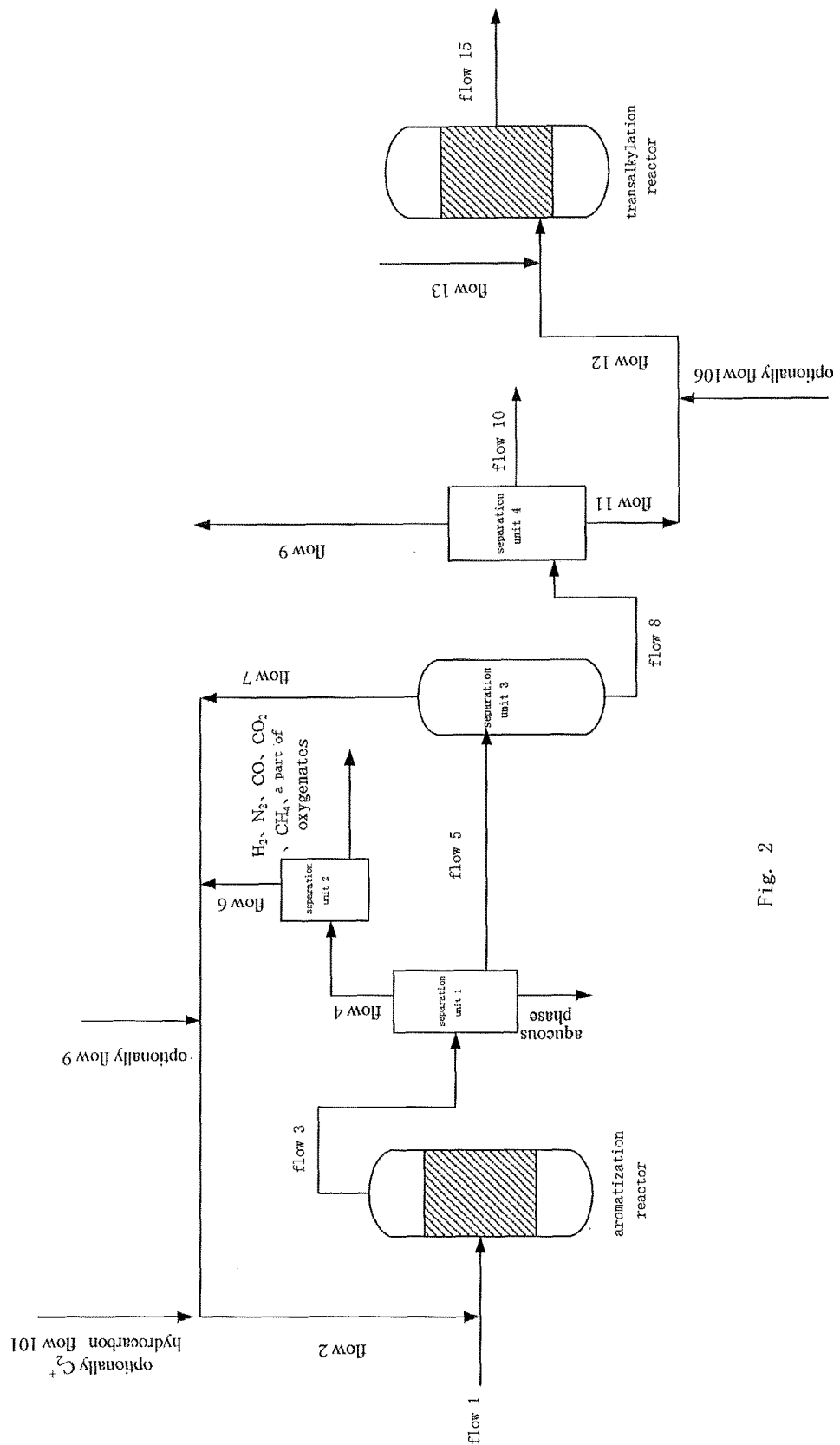
FIG. 2 is a flow chart of one embodiment of the present invention.

With reference to the reaction-separation flow chart of, for example, FIG. 2, it had the following steps.

a) contacting the methanol flow 1 in an aromatization reactor with a catalyst for reaction under the process conditions of a temperature of 550° C., a pressure of 2.0 MPa, a methanol weight space velocity of 4.0 h$^{-1}$ to obtain the hydrocarbons flow 3;
b) removing $CO_2$ and a part of oxygenates from the flow 3 through the separation unit 1 to obtain the gas phase non-aromatic hydrocarbons flow 4, the liquid hydrocarbons flow 5 containing aromatic hydrocarbons and the aqueous phase;
c) removing inorganic gases such as $H_2$, CO, $CO_2$, $N_2$ and the like, $CH_4$ and a part of oxygenates from the flow 4 through the separation unit 2 via pressure swing adsorption to obtain the $C_2^+$ hydrocarbons flow 6;
d) subjecting the hydrocarbons flow 5 to a non-precise rectification through the separation unit 3 to obtain the hydrocarbons flow 7 of aromatic hydrocarbons having less than or equal to 7 carbon numbers and the hydrocarbons flow 8 of aromatic hydrocarbons having more than 7 carbon numbers, and obtaining the hydrocarbons flow 9 containing non-aromatic hydrocarbon, the flow 10 containing $C_8$ aromatic hydrocarbon and the $C_9^+$ aromatic hydrocarbon flow 11 from the hydrocarbons flow 8 through the separation unit 4;
e) returning the above hydrocarbons flow 2 of aromatic hydrocarbons having less than or equal to 7 carbon numbers consisting of the $C_2^+$ hydrocarbons flow 6, the hydrocarbons flow 7 and the hydrocarbons flow 9 containing non-aromatic hydrocarbons and the $C_2^+$ hydrocarbons flow 101 outside the reaction-separation system to the above methanol flow 1 for further reaction, wherein the hydrocarbons flow 101 had a weight composition of 43% ethylene, 32% propylene, 20% 1-butene and 5% n-butane, and the $C_2^+$ hydrocarbons flow 101 and the methanol flow 1 has a weight ratio of 1:10;
f) forming the above $C_9^+$ aromatic hydrocarbon flow 12 with the above $C_9^+$ aromatic hydrocarbon flow 11, and contacting the $C_9^+$ aromatic hydrocarbon flow 12, the methylbenzene flow 13 outside the reaction-separation system through a dealkylation reactor under the conditions of a temperature of 350° C., a hydrogen pressure of 5.0 MPa and a weight space velocity of raw material(s) of 0.1 h$^{-1}$ with a catalyst to obtain the hydrocarbons flow 15 containing dimethylbenzene.

The aromatization reactor was of a fluidized-bed form and the transalkylation reactor was of a fixed-bed reactor form. The catalyst contained ZSM-5 molecular sieve active components having silicon oxide and aluminium oxide in a molar ratio of 10:1, wherein the catalyst was treated for 0.5 hour at 750° C. and a water vapor partial pressure of 100% before use.

In the present Example, the conversion rate of methanol was more than 99%; the yield of dimethylbenzene was 90.5% and the total yield of aromatic hydrocarbon was 98.9%, based on the weight of carbon and hydrogen of methanol.

Example 3

Figure 3:
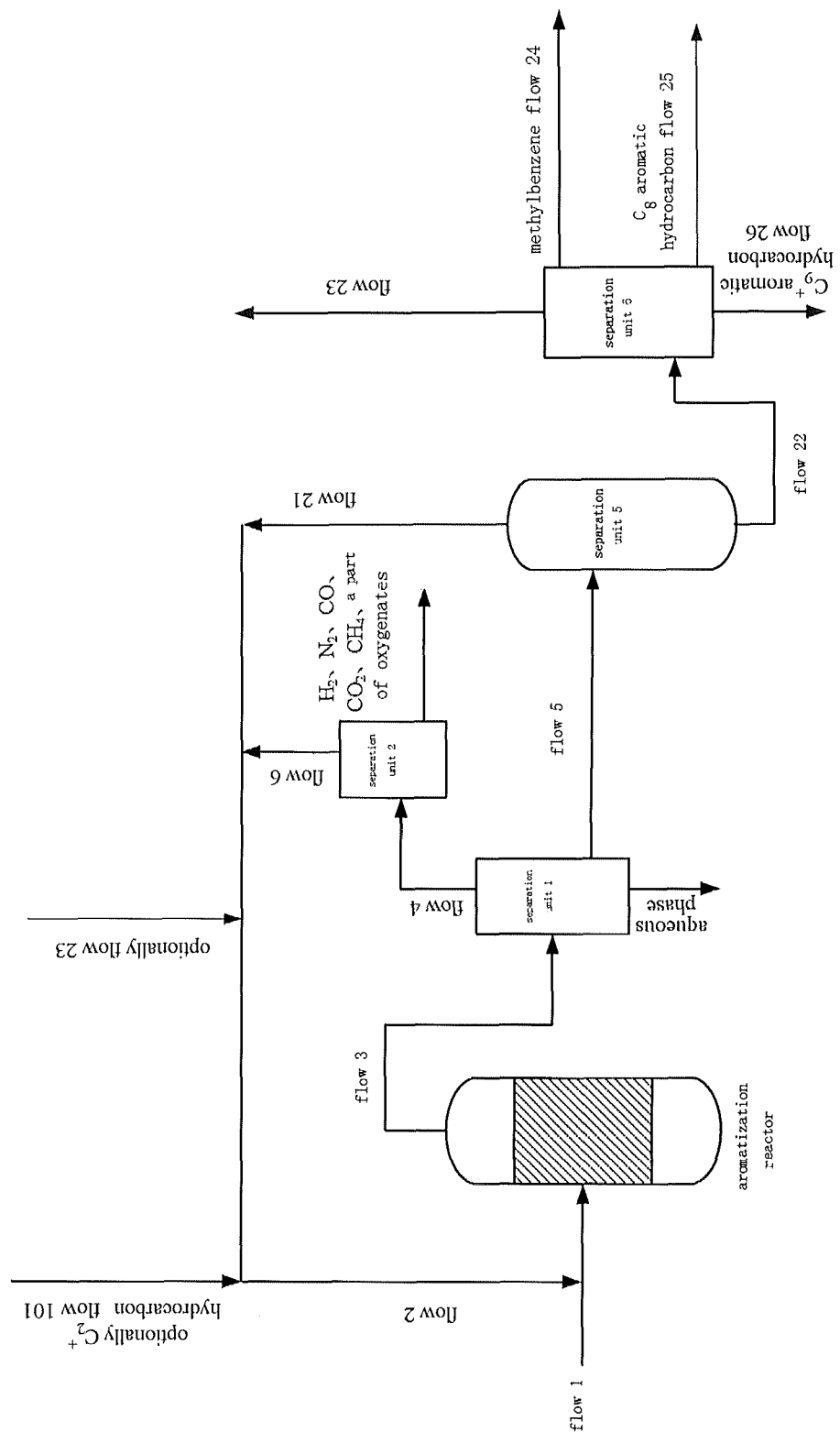
FIG. 3 is a flow chart of one embodiment of the present invention.

With reference to the reaction-separation flow chart of, for example, FIG. 3, it had the following steps:
a) contacting the dimethyl ether flow 1 in an aromatization reactor with a catalyst for reaction under the process conditions of a temperature of 480° C., a pressure of 0.3 MPa, a weight space velocity of raw material of 1.5 h$^{-1}$ to obtain the hydrocarbons flow 3;
b) removing $CO_2$ and a part of oxygenates from the flow 3 through the separation unit 1 to obtain the gas phase non-aromatic hydrocarbons flow 4, the liquid hydrocarbons flow 5 containing aromatic hydrocarbons and the aqueous phase;
c) removing inorganic gases such as $H_2$, CO, $CO_2$, $N_2$ and the like, $CH_4$ and a part of oxygenates from the flow 4 through the separation unit 2 via rectification to obtain the $C_2^+$ hydrocarbons flow 6;
d) subjecting the hydrocarbons flow 5 to a non-precise rectification through the separation unit 5 to obtain the hydrocarbons flow 21 of aromatic hydrocarbons having less than or equal to 6 carbon numbers and a hydrocarbons flow 22 of aromatic hydrocarbons having more than 6 carbon numbers, and obtaining the hydrocarbons flow 23 containing non-aromatic hydrocarbons, the methylbenzene flow 24, the flow 25 containing $C_8$ aromatic hydrocarbons and the $C_9^+$ aromatic hydrocarbon flow 26 from the flow 22 through the separation unit 6;
e) returning the above hydrocarbon flow 2 of aromatic hydrocarbons having less than or equal to 7 carbon numbers consisting of the $C_2^+$ hydrocarbons flow 6, the hydrocarbons flow 21 and the hydrocarbons flow 23 containing non-aromatic hydrocarbons to the above dimethyl ether flow 1 for further reaction.

The aromatization reactor was of a fluidized-bed reactor form. The catalyst contained ZSM-5 molecular sieve active components having silicon oxide and aluminium oxide in a molar ratio of 30:1, wherein the catalyst was treated for 120 hours at 400° C. and a water vapor partial pressure of 50% before use.

In the present Example, the conversion rate of dimethyl ether was more than 99%; the yield of dimethylbenzene was 82.5% and the total yield of aromatic hydrocarbon is 88.2%, based on the weight of carbon and hydrogen of dimethyl ether.

Example 4

Figure 4:
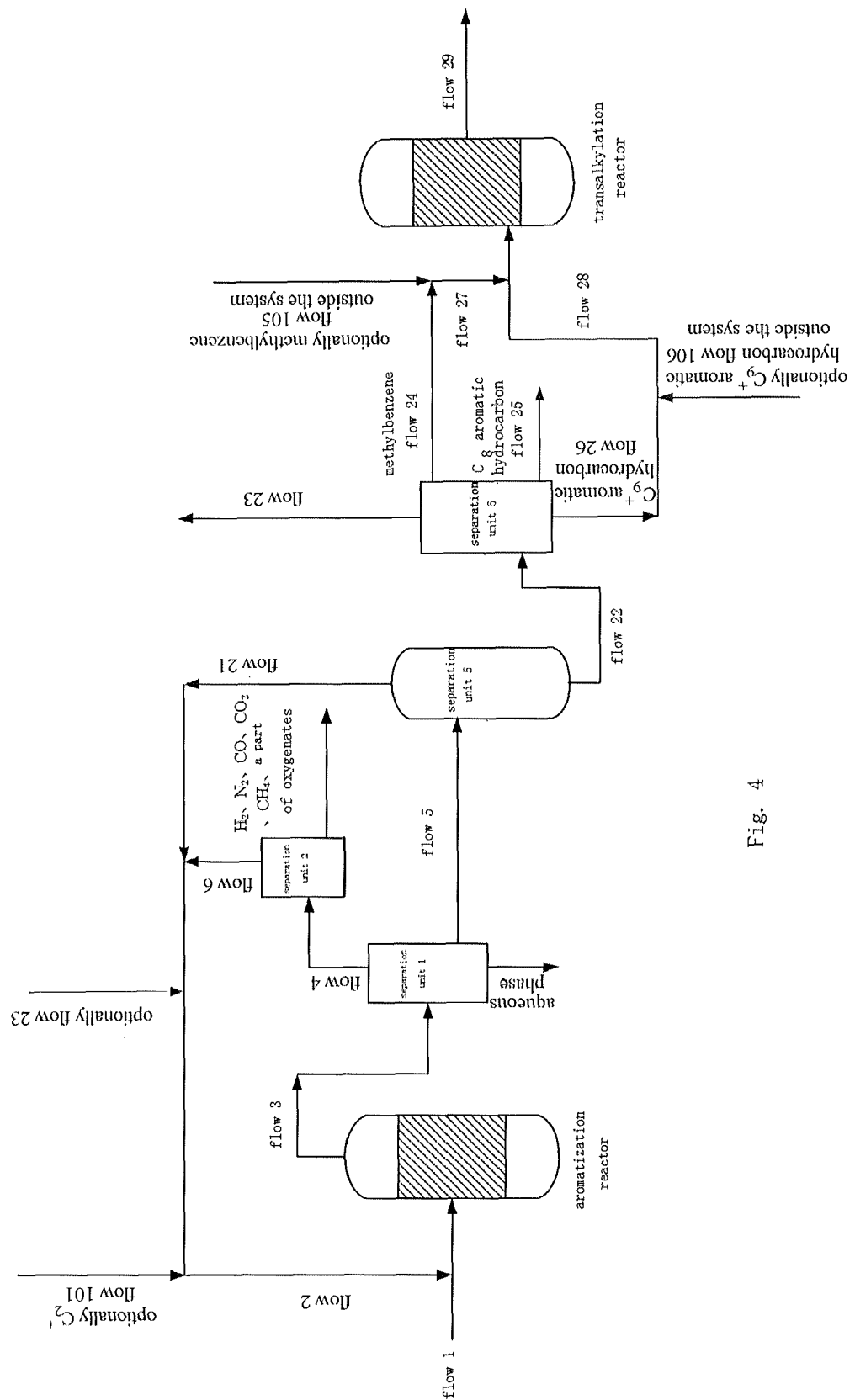
FIG. 4 is a flow chart of one embodiment of the present invention.

With reference to the reaction-separation flow chart of, for example, FIG. 4, it had the following steps.
a) contacting the dimethyl ether flow 1 in an aromatization reactor with a catalyst for reaction under the process conditions of a temperature of 520° C., a pressure of 0.3 MPa, a weight space velocity of raw material of 0.8 h$^{-1}$ to obtain the hydrocarbons flow 3;
b) removing $CO_2$ and a part of oxygenates from the flow 3 through the separation unit 1 to obtain the gas phase non-aromatic hydrocarbons flow 4, the liquid hydrocarbons flow 5 containing aromatic hydrocarbons and the aqueous phase;
c) removing inorganic gases such as $H_2$, CO, $CO_2$, $N_2$ and the like, $CH_4$ and a part of oxygenates from the flow 4 through the separation unit 2 via rectification to obtain the $C_2^+$ hydrocarbons flow 6;
d) subjecting the hydrocarbons flow 5 to a non-precise rectification through the separation unit 5 to obtain a hydrocarbons flow 21 of aromatic hydrocarbons having less than or equal to 6 carbon numbers and the hydrocarbons flow 22 of aromatic hydrocarbons having more than 6 carbon numbers, and obtaining the hydrocarbons flow 23 containing non-aromatic hydrocarbons, the methylbenzene flow 24, the flow 25 containing $C_8$ aromatic hydrocarbons and the $C_9^+$ aromatic hydrocarbon flow 26 from the flow 22 through the separation unit 6;
e) returning the above hydrocarbons flow 2 of aromatic hydrocarbons having less than or equal to 7 carbon numbers consisting of 95% by weight of the flow 6, the hydrocarbons flow 22 and the hydrocarbons flow 23 containing non-aromatic hydrocarbons to the above dimethyl ether flow 1 for further reaction;
f) the methylbenzene flow 24 and the methylbenzene flow 105 outside the reaction-separation system formed the mixed flow 27, wherein the weight ratio of the methylbenzene flow 105 to the methylbenzene flow 24 was 20:80, and the $C_9^+$ aromatic hydrocarbon flow 26 formed the $C_9^+$ aromatic hydrocarbon flow 28; contacting the mixed flow 27 and the $C_9^+$ aromatic hydrocarbon flow 28 in a transalkylation reactor under the reaction conditions of a temperature of 550° C., a hydrogen pressure of 0.5 MPa and a weight space velocity of raw material of 10 $h^{-1}$ with a catalyst to obtain the flow 29 containing dimethylbenzene.

The aromatization reactor was of a fluidized-bed reactor form. The catalyst contained ZSM-5 molecular sieve active components having silicon oxide and aluminium oxide in a molar ratio of 100:1, wherein the catalyst was treated for 60 hours at 550° C. and a water vapor partial pressure of 75% before use.

In the present Example, the conversion rate of dimethyl ether was more than 99%; the yield of dimethylbenzene was 88.3% and the total yield of aromatic hydrocarbons was 94.8%, based on the weight of carbon and hydrogen of dimethyl ether.

Example 5

Figure 5:
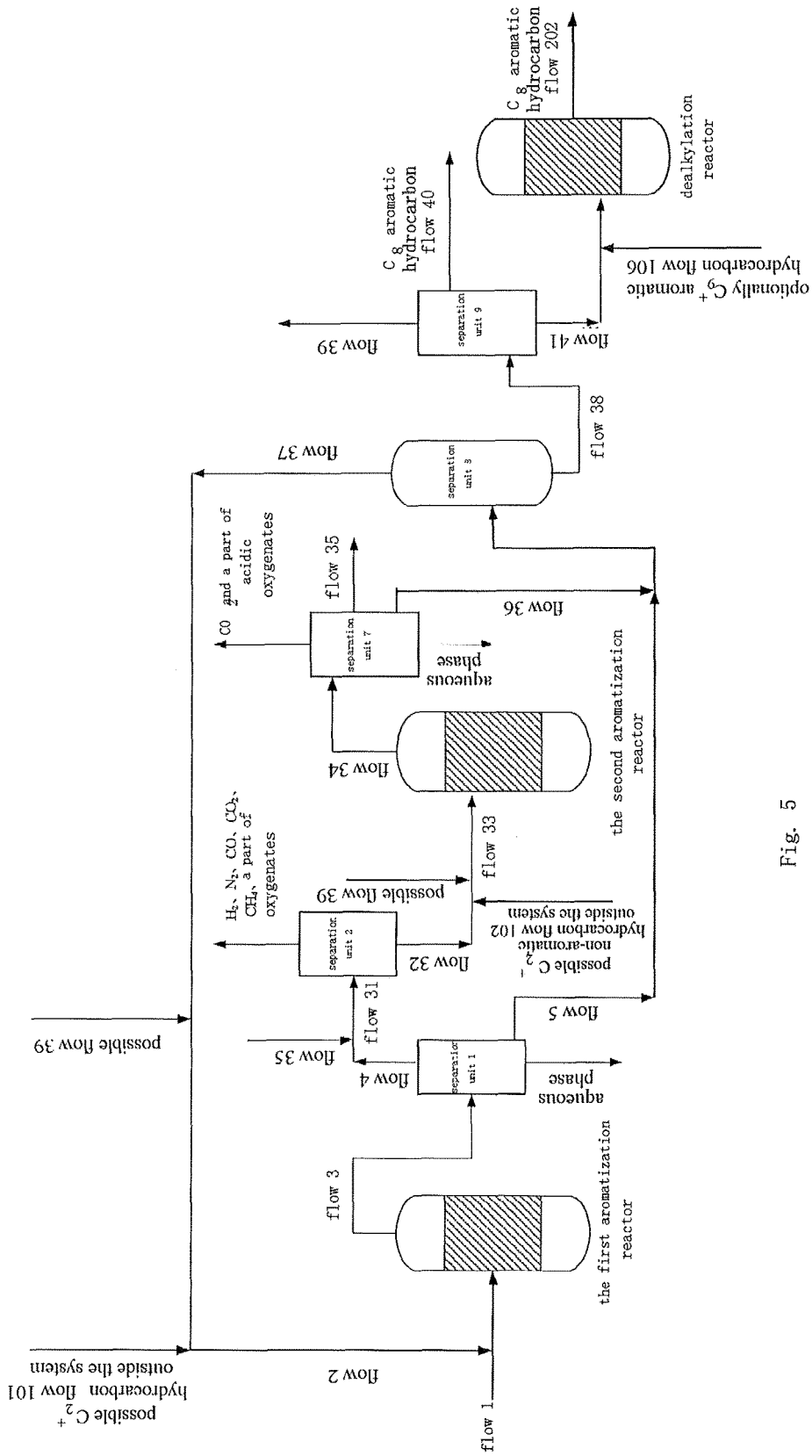
FIG. 5 is a flow chart of one embodiment of the present invention.

With reference to the reaction-separation flow chart of, for example, FIG. 5, it had the following steps:
h) contacting the methanol flow 1 in the first aromatization reactor with a catalyst for reaction under the process conditions of a temperature of 450° C., a pressure of 0.05 MPa, a weight space velocity of raw material of 1.0 $h^{-1}$ to obtain the hydrocarbons flow 3;
i) removing $CO_2$ and a part of acidic oxygenates from the flow 3 through the separation unit 1 to obtain the gas phase non-aromatic hydrocarbons flow 4, the liquid hydrocarbons flow 5 containing aromatic hydrocarbons and the aqueous phase;
j) removing inorganic gases such as $H_2$, CO, $CO_2$, $N_2$ and the like, $CH_4$ and a part of oxygenates from the hydrocarbons flow 31 through the separation unit 2 via $C_5$-$C_9$ gasoline absorption to obtain the $C_2^+$ non-aromatic hydrocarbons flow 32, wherein the hydrocarbon flow 31 was a mixed hydrocarbon flow of the flow 4 and the gas phase non-aromatic hydrocarbon flow 35;
k) contacting the mixed hydrocarbons flow 33 in the second aromatization reactor under the process conditions of a temperature of 450° C., a pressure of 0.1 MPa, a weight space velocity of raw material of 0.1 $h^{-1}$ to obtain the hydrocarbons flow 34, wherein the hydrocarbons flow 33 was a mixed hydrocarbons flow of the flow 32 and the flow I which was selected from a part or all of at least one of the $C_2^+$ non-aromatic hydrocarbons flow 102 outside the reaction-separation system and the flow 39;
l) removing $CO_2$ and a part of acidic oxygenates from the hydrocarbons flow 34 through the separation unit 7 to obtain the gas phase non-aromatic hydrocarbons flow 35, the liquid hydrocarbons flow 36 containing aromatic hydrocarbons and the aqueous phase;
m) separating the flow 5 and the flow 36 in the separation unit 8 through a non-precise rectification to obtain the hydrocarbon flow 37 of aromatic hydrocarbons having less than or equal to 7 carbon numbers and the hydrocarbons flow 38 of aromatic hydrocarbons having more than 7 carbon numbers, and separating the flow 38 through the separation unit 9 to obtain the flow 39 containing non-aromatic hydrocarbons, the $C_8$ aromatic hydrocarbon flow 40 and the $C_9^+$ aromatic hydrocarbon flow 41;
n) returning the hydrocarbons flow 2 of aromatic hydrocarbons having less than or equal to 7 carbon numbers formed by the flow 37 and the flow 39 to the methanol flow 1 for further reaction;
o) contacting the $C_9^+$ aromatic hydrocarbon flow 41 in a fixed-bed dealkylation reactor under the reaction conditions of a reaction temperature of 350° C., a reaction pressure of 3 MPa, a molar ratio of hydrogen to hydrocarbons of 10:1 and a hydrocarbons weight space velocity of 4 $h^{-1}$ with a Pt/ZSM-5 catalyst for reaction to obtain the $C_8$ aromatic hydrocarbon flow 202;

The first aromatization reactor was of a fluidized-bed reactor form and the second aromatization reactor was of a fixed-bed reactor form; the aromatization catalyst contained ZSM-5 molecular sieve active components having silicon oxide and aluminium oxide in a molar ratio of 100:1, wherein the catalyst was treated for 60 hours at 550° C. and a water vapor partial pressure of 75% before use.

In the present Example, the conversion rate of methanol was more than 99.9%; the yield of dimethylbenzene was 82.0% and the total yield of aromatic hydrocarbon was 89.7%, based on the weight of carbon and hydrogen of methanol.

Example 6

Figure 6:
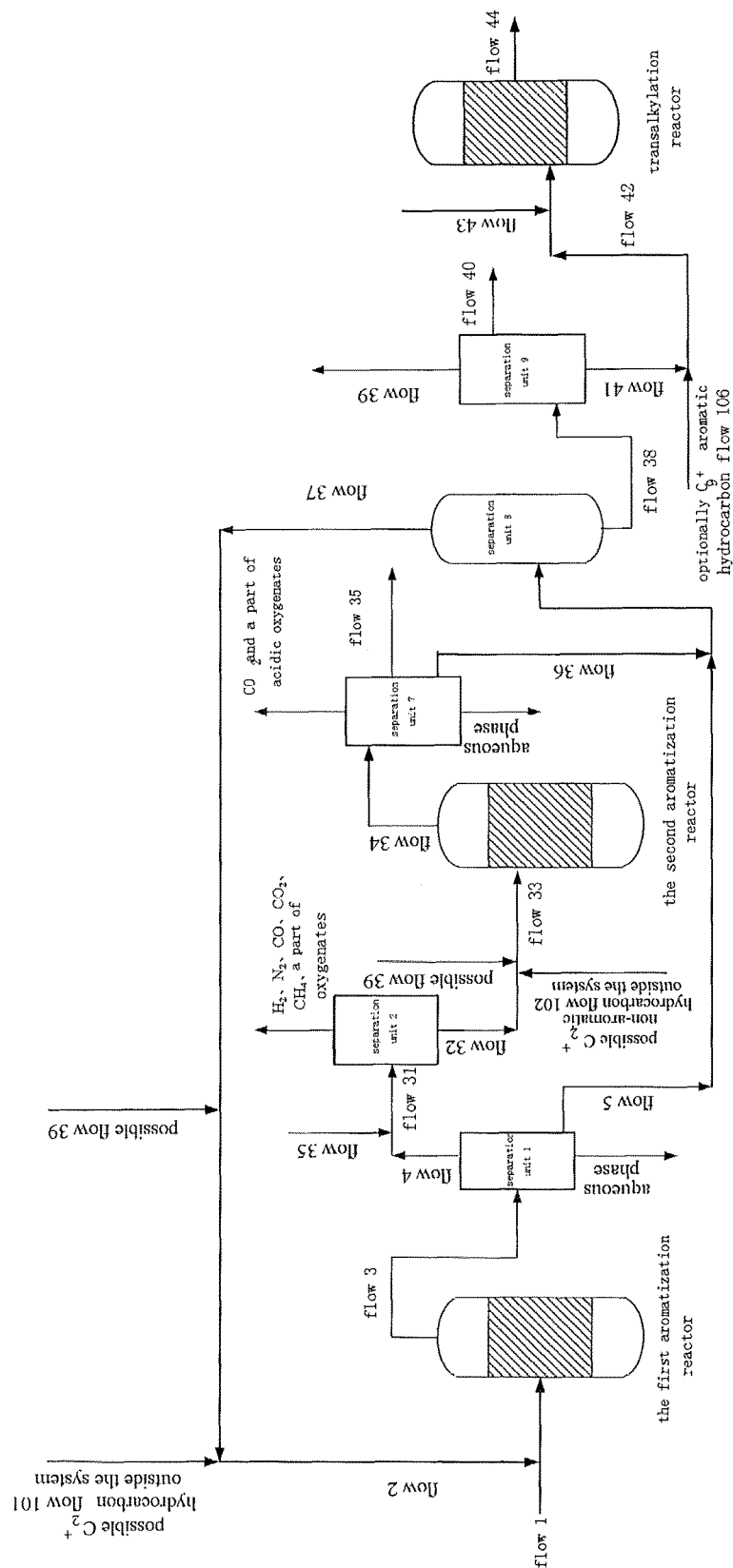
FIG. 6 is a flow chart of one embodiment of the present invention.

With reference to the reaction-separation flow chart of, for example, FIG. 6, it had the following steps.
h) contacting the methanol flow 1 in the first aromatization reactor with a catalyst for reaction under the process conditions of a temperature of 550° C., a pressure of 2.0 MPa, a weight space velocity of raw material of 4 $h^{-1}$ to obtain the hydrocarbons flow 3;
i) removing $CO_2$ and a part of acidic oxygenates from the flow 3 through the separation unit 1 to obtain the gas phase non-aromatic hydrocarbons flow 4, the liquid hydrocarbons flow 5 containing aromatic hydrocarbons and the aqueous phase;
j) removing inorganic gases such as $H_2$, CO, $CO_2$, $N_2$ and the like, $CH_4$ and a part of oxygenates from the hydrocarbons flow 31 through the separation unit 2 via rectification to obtain the $C_2^+$ non-aromatic hydrocarbons flow 32, wherein the hydrocarbons flow 31 was a mixed hydrocarbon flow of the flow 4 and 95% by weight of the flow 35;
k) contacting the hydrocarbons flow 33 in the second aromatization reactor under the process conditions of a temperature of 650° C., a pressure of 1.0 MPa, a weight space velocity of raw material of 4 $h^{-1}$ with a catalyst to obtain the hydrocarbons flow 34, wherein the hydrocarbons flow 33 was a mixed flow of the flow 32 and the $C_2^+$ non-aromatic hydrocarbons flow 102 whose weight composition was 35% ethylene, 5% ethane, 29% propylene, 12% propane, 11%1-butene, 7% n-butane, and the weight ratio of the $C_2^+$ non-aromatic hydrocarbon flow 102 to the flow 32 was 0.5:1;
l) removing $CO_2$ and a part of acidic oxygenate to obtain the gas phase non-aromatic hydrocarbon flow 35, the liquid phase hydrocarbons flow 36 containing aromatic hydrocarbons and the aqueous phase from the hydrocarbons flow 34 through the separation unit 7;
m) separating the flow 5 and the flow 36 in the separation unit 8 through a non-precise rectification to obtain the hydrocarbons flow 37 of aromatic hydrocarbons having less than or equal to 7 carbon numbers and the hydrocarbons flow 38 having more than 7 carbon numbers, and separating the flow 38 through the separation unit 9 to obtain the flow 39 containing non-aromatic hydrocarbons, the $C_8$ aromatic hydrocarbon flow 40 and the $C_9^+$ aromatic hydrocarbon flow 41;

n) returning the hydrocarbons flow 2 of aromatic hydrocarbons having less than or equal to 7 carbon numbers formed by the flow 37 and the flow 39 to the methanol flow 1 for further reaction;

o) forming a $C_9^+$ aromatic hydrocarbon flow 42 by the flow 41, and contacting the $C_9^+$ aromatic hydrocarbon flow 42 and the methylbenzene 43 outside the reaction-separation system in the dealkylation reactor under a reaction temperature of 400° C., a reaction pressure of 3.0 MPa, a weight space velocity of raw material of 4 h$^{-1}$ with a catalyst for reaction to obtain a $C_8$ aromatic hydrocarbon flow 44;

wherein, both the first aromatization reactor and the second aromatization reactor were of a fluidized-bed reactor form and the same catalyst were used, wherein the catalyst contained ZSM-11 molecular sieve active components having silicon oxide and aluminium oxide in a molar ratio of 75:1 and the catalyst was treated for 16 hours at 700° C. and a water vapor partial pressure of 30% before use.

In the present Example, the conversion rate of methanol was more than 99.9%; the yield of dimethylbenzene was 91.7% and the total yield of aromatic hydrocarbon was 99.2%, based on the weight of carbon and hydrogen of methanol.

Example 7

Figure 7:
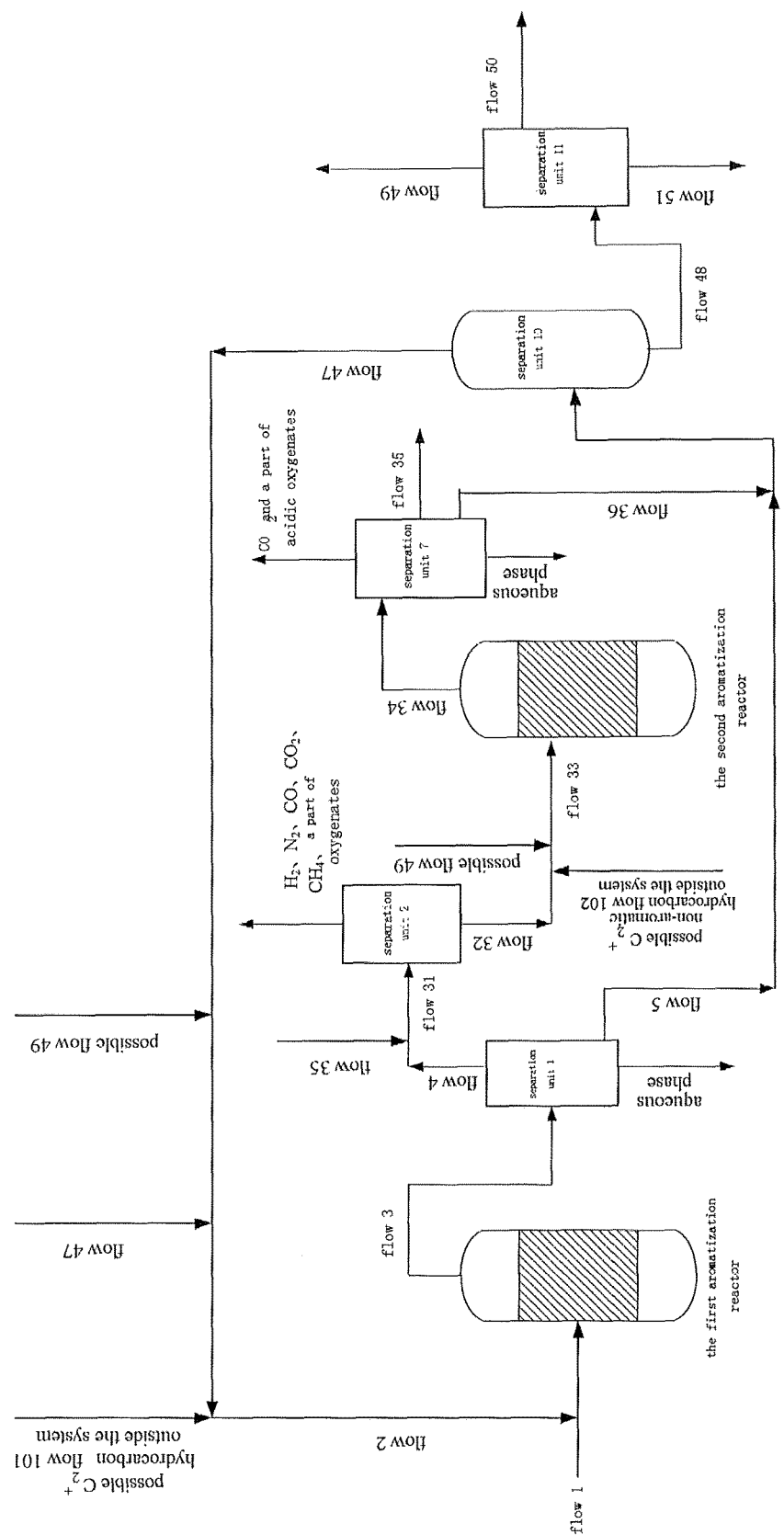
FIG. 7 is a flow chart of one embodiment of the present invention.

With reference to the reaction-separation flow chart of, for example, FIG. 7, it had the following steps:

h) contacting an methanol flow 1 in the first aromatization reactor with a catalyst for reaction under the process conditions of a temperature of 500° C., a pressure of 0.5 MPa, a weight space velocity of raw material of 0.8 h$^{-1}$ to obtain the hydrocarbons flow 3;

i) removing $CO_2$ and a part of acidic oxygenates from the flow 3 through the separation unit 1 to obtain the gas phase non-aromatic hydrocarbons flow 4, the liquid hydrocarbons flow 5 containing aromatic hydrocarbons and the aqueous phase;

j) removing inorganic gases such as $H_2$, CO, $CO_2$, $N_2$ and the like, $CH_4$ and a part of oxygenates from the hydrocarbons flow 31 through the separation unit 2 via rectification to obtain the $C_2^+$ non-aromatic hydrocarbon flow 32, wherein the hydrocarbons flow 31 was a mixed hydrocarbon flow of the flow 4 and the gas phase non-aromatic hydrocarbons flow 35;

k) contacting the hydrocarbons flow 33 in the second aromatization reactor under the process conditions of a temperature of 600° C., a pressure of 0.3 MPa, a weight space velocity of raw material of 1.0 h$^{-1}$ with a catalyst to obtain the hydrocarbons flow 34, wherein the hydrocarbons flow 33 was from a flow 32;

l) removing $CO_2$ and a part of acidic oxygenate(s) to obtain the gas phase non-aromatic hydrocarbon flow 35, the liquid phase hydrocarbon flow 36 containing aromatic hydrocarbons and the aqueous phase from the hydrocarbons flow 34 through the separation unit 7;

m) separating the flow 5 and the flow 36 in the separation unit 10 through a non-precise rectification to obtain the hydrocarbons flow 47 of aromatic hydrocarbons having less than or equal to 7 carbon numbers and the hydrocarbons flow 48 having more than 7 carbon numbers, and separating the flow 48 through the separation unit 11 to obtain the flow 49 containing non-aromatic hydrocarbons, the $C_8$ aromatic hydrocarbon flow 50 and the $C_9^+$ aromatic hydrocarbon flow 51;

n) returning the hydrocarbons flow 2 of aromatic hydrocarbons having less than or equal to 7 carbon numbers formed by the flow 47 and the flow 49 to the methanol flow 1 for further reaction;

wherein, both the first aromatization reactor and the second aromatization reactor were of a moving-bed reactor form and the same catalysts were used, wherein the catalyst contained ZSM-5 molecular sieve active components having silicon oxide and aluminium oxide in a molar ratio of 150:1 and the catalyst was treated for 24 hours at 600° C. and a water vapor partial pressure of 60% before use.

In the present Example, the conversion rate of methanol was more than 99.9%; the yield of dimethylbenzene was 82.9% and the total yield of aromatic hydrocarbon was 88.5%, based on the weight of carbon and hydrogen of methanol.

Example 8

Figure 8:
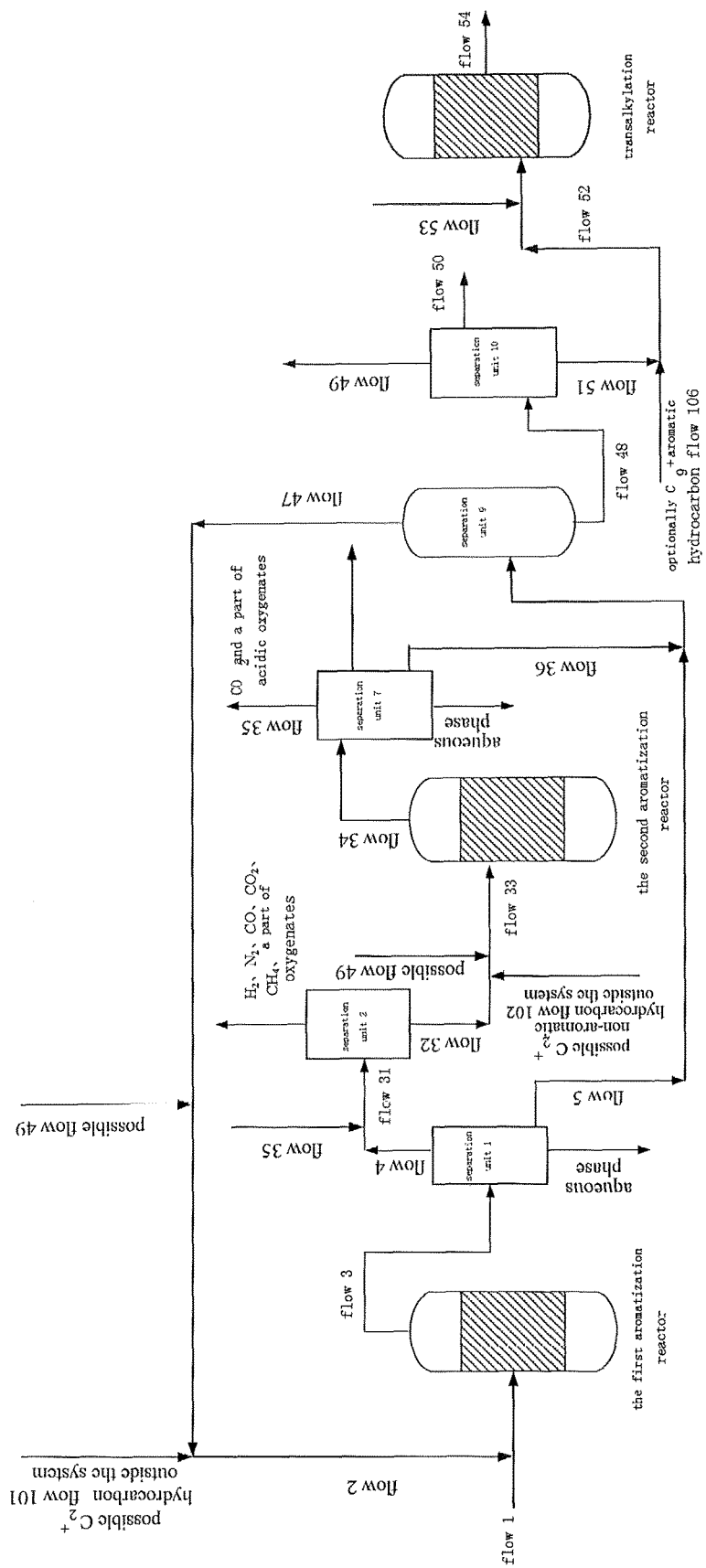
FIG. 8 is a flow chart of one embodiment of the present invention.
Figure 10:
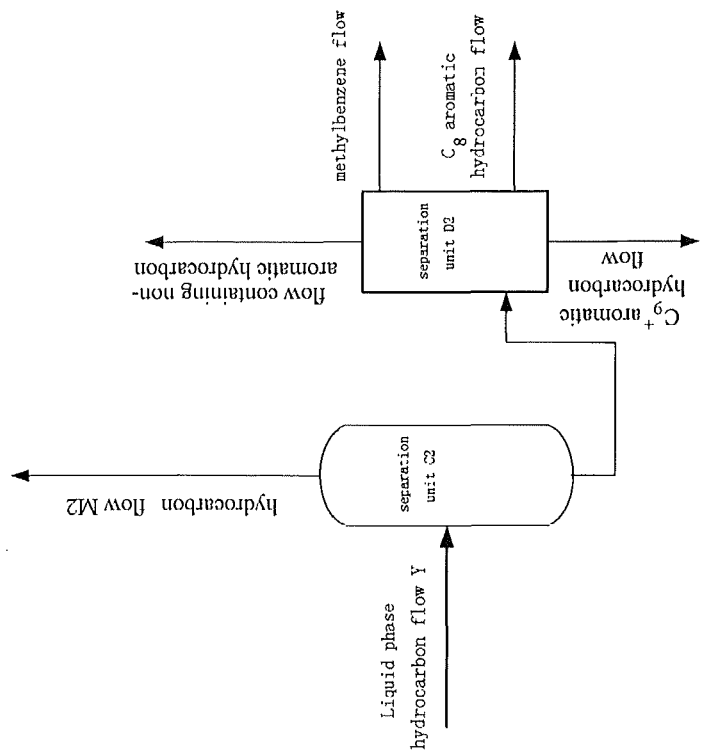
FIG. 10 is a flow chart of the separation manner of the flow Y of the present invention.
Figure 9:
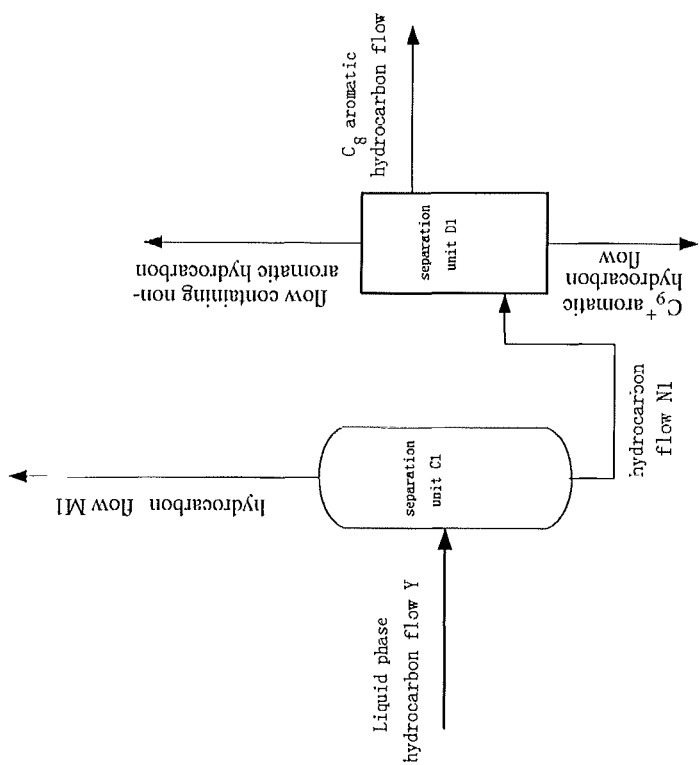
FIG. 9 is a flow chart of the separation manner of the flow Y of the present invention.

With reference to the reaction-separation flow chart of, for example, FIG. 8, it had the following steps.

h) contacting the methanol flow 1 and the hydrocarbons flow 2 of aromatic hydrocarbons having less than or equal to 7 carbon numbers in the first aromatization reactor with a catalyst for reaction under the process conditions of a temperature of 480° C., a pressure of 0.4 MPa, a weight space velocity of raw material of 0.6 h$^{-1}$ to obtain the hydrocarbons flow 3;

i) removing $CO_2$ and a part of acidic oxygenates from the flow 3 through the separation unit 1 to obtain the gas phase non-aromatic hydrocarbons flow 4, the liquid hydrocarbons flow 5 containing aromatic hydrocarbons and the aqueous phase;

j) removing inorganic gases such as $H_2$, CO, $CO_2$, $N_2$ and the like, $CH_4$ and a part of oxygenates from the hydrocarbons flow 31 through the separation unit 2 via pressure swing adsorption to obtain the $C_2^+$ non-aromatic hydrocarbons flow 32, the hydrocarbons flow 31 is a mixed hydrocarbons flow of the flow 4 and the flow 35;

k) contacting the hydrocarbons flow 33 in the second aromatization reactor under the process conditions of a temperature of 610° C., a pressure of 0.3 MPa, a weight space velocity of raw material of 0.8 h$^{-1}$ with a catalyst to obtain the hydrocarbons flow 34, wherein the hydrocarbons flow 33 was the flow 32;

l) removing $CO_2$ and a part of acidic oxygenates to obtain the gas phase non-aromatic hydrocarbon flow 35, the liquid phase hydrocarbons flow 36 containing aromatic hydrocarbons and the aqueous phase from the hydrocarbons flow 34 through the separation unit 7;

m) separating the flow 5 and the flow 36 in the separation unit 9 through a non-precise rectification to obtain the hydrocarbons flow 47 of aromatic hydrocarbon having less than or equal to 7 carbon numbers and the hydrocarbons flow 48 having more than 7 carbon numbers, and separating the flow 48 through the separation unit 10 to obtain the flow 49 containing non-aromatic hydrocarbons, the $C_8$ aromatic hydrocarbon flow 50 and the $C_9^+$ aromatic hydrocarbon flow 51;

n) returning the hydrocarbons flow 2 of aromatic hydrocarbons having less than or equal to 7 carbon numbers formed by the flow 47 and the flow 49 to the methanol flow 1 for further reaction;

o) the mixed $C_9^+$ aromatic hydrocarbon flow 52, which was formed by the flow 51 and the $C_9^+$ aromatic hydrocarbon flow 106 outside the reaction-separation system, reacted with the methylbenzene flow 53 outside the reaction-separation system through a transalkylation reactor under a reaction temperature of 450° C., a hydrogen pressure of 4.0 MPa, a weight space velocity of raw material of 2 $h^{-1}$ to obtain the $C_8$ aromatic hydrocarbon flow 54, wherein the weight ratio of the methylbenzene flow 53 outside the reaction-separation system to the $C_9^+$ aromatic hydrocarbon flow 52 was 1:5 and the weight ratio of the flow 106 to the flow 51 was 1:5;

wherein, both the first aromatization reactor and the second aromatization reactor were of a fluidized-bed reactor form, the transalkylation reactor was of a fixed-bed form, and they comprised the same catalysts, wherein the catalyst contained ZSM-5 molecular sieve active components having silicon oxide and aluminium oxide in a molar ratio of 150:1 and the catalyst was treated for 24 hours at 600° C. and a water vapor partial pressure of 60% before use.

In the present Example, the conversion rate of methanol was more than 99.9%; the yield of dimethylbenzene was 87.6% and the total yield of aromatic hydrocarbon was 95.2%, based on the weight of carbon and hydrogen of methanol.

Comparative Example 1

The reaction-separation procedure of producing aromatic hydrocarbons with an oxygenate comprised one aromatization reactor. The byproducts, i.e. non-aromatic hydrocarbons and benzene and methylbenzene, were taken as product directly, and were not subjected to a cycle conversion to aromatic hydrocarbons; the raw materials, the forms of aromatization reactors and the reaction conditions were the same as those of Example 1. The conversion rate of methanol was more than 99.9%, the total yield of aromatic hydrocarbon was 49.6% and the yield of dimethylbenzene was 29.8%.

Comparative Example 2

The reaction-separation procedure of producing aromatic hydrocarbons with an oxygenate comprised one aromatization reactor; only benzene and methylbenzene in the product were returned to the reactor and converted to dimethylbenzene through alkylation. The raw materials, the forms of aromatization reactors, the reaction conditions and the operation conditions were the same as those of Example 3. The conversion rate of methanol was more than 99.9%, the total yield of aromatic hydrocarbon was 53.4% and the yield of dimethylbenzene was 35.2%.

The invention claimed is:

1. A method for producing an aromatic hydrocarbon with an oxygenate as raw material, comprising
   i) reacting an oxygenate in at least one aromatization reactor to obtain an aromatization reaction product;
   ii) separating the aromatization reaction product through a separation unit A, to obtain a gas phase hydrocarbons flow X and a liquid phase hydrocarbons flow Y;
   iii) separating the gas phase hydrocarbons flow X through a separation unit B, to remove at least one substance and/or a part of the oxygenate and to obtain a hydrocarbons flow X1 containing a non-aromatic hydrocarbon; or
   separating the gas phase hydrocarbons flow X through a separation unit B to remove at least one substance and/or a part of the oxygenate and to obtain a remaining part, subjecting the remaining part to a second aromatization reaction in a second aromatization reactor, and separating the second aromatization reaction product through the separation unit A, to obtain a flow X2 containing a non-aromatic hydrocarbon and a flow X3 containing an aromatic hydrocarbon;
   iv) subjecting the liquid phase hydrocarbons flow Y and optionally the flow X3 containing an aromatic hydrocarbon to a non-precise rectification in a separation unit C, to obtain a mixed hydrocarbons flow M of an aromatic hydrocarbon having less than or equal to 7 carbon numbers and a flow N of residual hydrocarbons;
   v) separating the flow N of the residual hydrocarbons through a separation unit D, to obtain a flow K containing a non-aromatic hydrocarbon, a $C_8$ aromatic hydrocarbon flow J and a $C_9^+$ aromatic hydrocarbon flow L;
   vi) recycling one of the hydrocarbons flow X1 containing a non-aromatic hydrocarbon and the flow X2 containing a non-aromatic hydrocarbon, the mixed hydrocarbons flow M of an aromatic hydrocarbon having less than or equal to 7 carbon numbers and/or a part or all of the flow K containing a non-aromatic hydrocarbon, optionally with an additional $C_2^+$ hydrocarbons flow, to the above oxygenate; or
   recycling one of the hydrocarbons flow X1 containing a non-aromatic hydrocarbon and the flow X2 containing a non-aromatic hydrocarbon, the mixed hydrocarbons flow M of an aromatic hydrocarbon having less than or equal to 7 carbon numbers and/or a part or all of the flow K containing a non-aromatic hydrocarbon to the aromatization reactor in iii);
   vii) optionally, reacting the $C_9^+$ aromatic hydrocarbons flow L in at least one reactor selected from a transalkylation reactor and a dealkylation reactor to obtain a $C_8$ aromatic hydrocarbon flow L1.

2. The method for producing an aromatic hydrocarbon with an oxygenate as raw material according to claim 1, wherein the liquid phase hydrocarbons flow Y is separated by one of the following two manners:
   1) flow Y enters a separation unit C1 and is separated by a non-precise rectification to obtain a mixed hydrocarbons flow M1 of aromatic hydrocarbons having less than or equal to 6 carbon numbers and a hydrocarbons flow N1 having more than 6 carbon numbers, and the hydrocarbons flow N1 enters a separation unit D1 to obtain a $C_8$ aromatic hydrocarbon flow and a $C_9^+$ aromatic hydrocarbon flow;
   2) flow Y enters a separation unit C2 and is separated by a non-precise rectification to obtain a mixed hydrocarbons flow M2 of aromatic hydrocarbons having less than or equal to 7 carbon numbers and a hydrocarbons flow N2 having more than 7 carbon numbers, and the hydrocarbons flow N2 enters a separation unit D2 to obtain a $C_8$ aromatic hydrocarbon flow and a $C_9^+$ aromatic hydrocarbon flow.

3. The method for producing an aromatic hydrocarbon with an oxygenate as raw material according to claim 1, wherein a part or all of the non-aromatic hydrocarbon flow and the flow of the oxygenate come into contact with a catalyst for reaction in the same aromatization reactor or by entering different aromatization reactors; at least one reactor selected from the group consisting of a transalkylation reactor and a dealkylation reactor in the method is used for converting a $C_9^+$ aromatic hydrocarbon flow in the product of aromatic hydrocarbons to dimethylbenzene; the reaction conditions for said transalkylation reactor are a temperature of 350 to 550° C., a reaction pressure of 0.1 to 5.0 MPa, a molar ratio of hydrogen/hydrocarbon of 1.5:1 to 200:1, a weight space velocity of raw material of 0.1 to 5 h$^{-1}$; the reaction conditions of said dealkylation reactor are a reaction temperature of 300 to 800° C., a molar ratio of hydrogen/hydrocarbon of 0.1 to 200:1 and a weight space velocity of the hydrocarbons of 0.5 to 10 h$^{-1}$.

4. The method for producing an aromatic hydrocarbon with an oxygenate as raw material according to claim 1, comprising only one aromatization reactor, said method comprising the following steps:
  a) under process conditions of a temperature of 400 to 550° C., a pressure of 0.01 to 2.0 MPa and a weight space velocity of raw material(s) of 0.1 to 4 h$^{-1}$, contacting a flow of oxygenate(s) with a catalyst for reaction in the aromatization reactor to obtain a first hydrocarbons flow;
  b) removing $CO_2$ and a part of oxygenate(s) from said first hydrocarbons flow through a first separation unit to obtain a gas phase non-aromatic hydrocarbons flow, a liquid phase hydrocarbons flow containing an aromatic hydrocarbon and an aqueous phase;
  c) removing at least one substance and a part of oxygenate(s) from said gas phase non-aromatic hydrocarbons flow through a second separation unit to obtain a $C_2^+$ hydrocarbons flow;
  d) further separating the liquid phase hydrocarbons flow containing an aromatic hydrocarbon according to one of the following four manners:
  d1) subjecting the liquid phase hydrocarbons flow containing an aromatic hydrocarbon to non-precise rectification through a third separation unit to obtain a second hydrocarbon flow of aromatic hydrocarbons having less than or equal to 7 carbon numbers and a third hydrocarbon flow of aromatic hydrocarbons having more than 7 carbon numbers, and separating said third hydrocarbons flow through a fourth separation unit to obtain a fourth hydrocarbons flow, a flow containing $C_8$ aromatic hydrocarbon and a $C_9^+$ aromatic hydrocarbon flow, and reacting said $C_9^+$ aromatic hydrocarbon flow in a dealkylation reactor to obtain a $C_8$ aromatic hydrocarbon flow;
  obtaining a fifth hydrocarbons flow of aromatic hydrocarbons having less than or equal to 7 carbon numbers from the second hydrocarbons flow and a part or all of the $C_2^+$ hydrocarbons flow, wherein said fifth hydrocarbons flow further optionally comprises a part or all of at least one selected from the fourth hydrocarbons flow and a $C_2^+$ hydrocarbons flow outside the reaction-separation system; and
  returning said fifth hydrocarbons flow to the oxygenate(s) flow for further reaction;
  d2) subjecting the liquid phase hydrocarbons flow containing an aromatic hydrocarbon to a non-precise rectification through a third separation unit to obtain a second hydrocarbon flow of aromatic hydrocarbons having less than or equal to 7 carbon numbers and a third hydrocarbons flow of aromatic hydrocarbons having more than 7 carbon numbers, and obtaining a fourth hydrocarbons flow containing non-aromatic hydrocarbons, a flow containing $C_8$ aromatic hydrocarbons and a first $C_9^+$ aromatic hydrocarbon flow from said third hydrocarbons flow through a fourth separation unit;
  obtaining a sixth hydrocarbon flow containing dimethylbenzene from a second $C_9^+$ aromatic hydrocarbon flow and a methylbenzene flow outside the reaction-separation system through a transalkylation reactor, wherein the second $C_9^+$ aromatic hydrocarbon flow is selected from one of a part or all of the first $C_9^+$ aromatic hydrocarbon flow or a mixture of a part or all of the first $C_9^+$ aromatic hydrocarbon flow and a $C_9^+$ aromatic hydrocarbon flow outside the reaction-separation system;
  obtaining a fifth hydrocarbons flow of aromatic hydrocarbon having less than or equal to 7 carbon numbers from the second hydrocarbons flow and a part or all of the $C_2^+$ hydrocarbons flow, wherein said fifth hydrocarbons flow further optionally comprises a part or all of at least one selected from the fourth hydrocarbons flow and a $C_2^+$ hydrocarbons flow outside the reaction-separation system; and
  returning said fifth hydrocarbons flow to the oxygenate(s) flow for further reaction;
  d3) subjecting the liquid phase hydrocarbons flow containing an aromatic hydrocarbon to a non-precise rectification through a fifth separation unit to obtain a seventh hydrocarbon flow of aromatic hydrocarbon having less than or equal to 6 carbon numbers and an eighth hydrocarbons flow of aromatic hydrocarbon having more than 6 carbon numbers,
  obtaining a ninth hydrocarbons flow containing non-aromatic hydrocarbons, a first methylbenzene flow, a flow containing $C_8$ aromatic hydrocarbons and a $C_9^+$ aromatic hydrocarbon flow from said eighth flow through a sixth separation unit;
  obtaining a fifth hydrocarbons flow of aromatic hydrocarbons having less than or equal to 7 carbon numbers from a part or all of the $C_2^+$ hydrocarbons flow and the seventh hydrocarbons flow, wherein said fifth hydrocarbons flow further optionally comprises a part or all of at least one selected from the ninth hydrocarbons flow and a $C_2^+$ hydrocarbons flow outside the reaction-separation system; and
  returning said fifth hydrocarbons flow to the oxygenate flow for further reaction;
  d4) subjecting the liquid phase hydrocarbons flow containing an aromatic hydrocarbon to a non-precise rectification through a fifth separation unit to obtain a seventh hydrocarbons flow of aromatic hydrocarbons having less than or equal to 6 carbon numbers and an eighth hydrocarbons flow of aromatic hydrocarbons having more than 6 carbon numbers,
  obtaining a ninth hydrocarbon flow containing non-aromatic hydrocarbons, a first methylbenzene flow, a flow containing $C_8$ aromatic hydrocarbons and a first $C_9^+$ aromatic hydrocarbon flow from said eighth hydrocarbons flow through a sixth separation unit;
  contacting a methylbenzene flow and a second $C_9^+$ aromatic hydrocarbon flow with a catalyst in a transalkylation reactor to obtain a flow containing dimethylbenzene, wherein said second methylbenzene flow is selected from one of a part or all of the first methylbenzene flow or a mixed flow of a part or all of the first methylbenzene flow and a methylbenzene flow outside the reaction-separation system, and said second $C_9^+$ aromatic hydrocarbon flow is selected from one of a part or all of the first $C_9^+$ aromatic hydrocarbon flow or a mixed flow of a part or all of the first $C_9^+$ aromatic hydrocarbon flow and a $C_9^+$ aromatic hydrocarbon flow outside the reaction-separation system;
  obtaining a fifth hydrocarbons flow of aromatic hydrocarbons having less than or equal to 7 carbon numbers from a part or all of the $C_2^+$ hydrocarbon flow and the seventh hydrocarbons flow, wherein said fifth hydrocarbons flow further optionally comprises a part or all of at least one selected from the ninth hydrocarbon flow and a $C_2^+$ hydrocarbons flow outside the reaction-separation system; and returning said fifth hydrocarbons flow to the oxygenate(s) flow for further reaction.

5. The method for producing an aromatic hydrocarbon with an oxygenate as raw material according to claim 1, comprising two aromatization reactors, said method comprising the following steps:

h) under process conditions of a temperature of 400 to 550° C., a reaction pressure of 0.01 to 2.0 MPa and a weight space velocity of raw material(s) of 0.1 to 4 $h^{-1}$, contacting a flow of oxygenate(s) with a catalyst for reaction in a first aromatization reactor to obtain a first hydrocarbons flow;

i) removing $CO_2$ and a part of acidic oxygenate to obtain a first gas phase non-aromatic hydrocarbon flow, a first liquid phase hydrocarbons flow containing aromatic hydrocarbons and an aqueous phase from the first hydrocarbons flow through a first separation unit;

j) removing gas and a part of oxygenate(s) from a second hydrocarbons flow through a second separation unit to obtain a $C_2^+$ non-aromatic hydrocarbons flow, wherein the second hydrocarbons flow is a mixed hydrocarbons flow of the first gas phase non-aromatic hydrocarbon flow and a third flow;

k) under process conditions of a temperature of 450 to 650° C., a reaction pressure of 0.01 to 2.0 MPa and a weight space velocity of raw material(s) of 0.1 to 4 $h^{-1}$, contacting a fourth hydrocarbons flow with a catalyst in a second aromatization reactor to obtain a fifth hydrocarbons flow, wherein said fourth hydrocarbons flow is selected from a mixed hydrocarbons flow of the $C_2^+$ non-aromatic hydrocarbons flow and a flow I, wherein the flow I is selected from a part or all of at least one of a $C_2^+$ non-aromatic hydrocarbon flow outside the reaction-separation system and a sixth flow;

l) removing $CO_2$ and a part of acidic oxygenate to obtain a second gas phase non-aromatic hydrocarbon flow, a second liquid phase hydrocarbons flow containing aromatic hydrocarbons and an aqueous phase from the fifth hydrocarbons flow through a seventh separation unit;

m) further separating the first liquid phase hydrocarbons flow and the second liquid phase hydrocarbons flow according to one of the following four manners:

m1) separating the first liquid phase hydrocarbons flow and the second liquid phase hydrocarbons flow in an eighth separation unit by a non-precise rectification to obtain a seventh hydrocarbons flow of aromatic hydrocarbons having less than or equal to 7 carbon numbers and an eighth hydrocarbons flow of aromatic hydrocarbons having more than 7 carbon numbers, and separating said eighth hydrocarbons flow through a ninth separation unit to obtain the ninth flow containing non-aromatic hydrocarbons, a first $C_8$ aromatic hydrocarbon flow and a first $C_9^+$ aromatic hydrocarbon flow, reacting said first $C_9^+$ aromatic hydrocarbon flow or a mixed hydrocarbons flow of the first $C_9^+$ aromatic hydrocarbon flow and optionally a second $C_9^+$ aromatic hydrocarbon flow in a dealkylation reactor to obtain a second $C_8$ aromatic hydrocarbon flow;

obtaining a tenth hydrocarbons flow of aromatic hydrocarbons having less than or equal to 7 carbon numbers from the seventh hydrocarbons flow and a flow H, wherein said flow H is selected from at least one of a $C_2^+$ hydrocarbons flow outside the reaction-separation system and the ninth flow; and returning said tenth hydrocarbons flow to the oxygenate(s) flow for further reaction;

m2) separating the first liquid phase hydrocarbons flow and the second liquid phase hydrocarbons flow in an eighth separation unit by a non-precise rectification to obtain a seventh hydrocarbons flow of aromatic hydrocarbons having less than or equal to 7 carbon numbers and an eighth hydrocarbons flow having more than 7 carbon numbers, and separating said eighth hydrocarbons flow through a ninth separation unit to obtain the ninth flow containing non-aromatic hydrocarbons, a $C_8$ aromatic hydrocarbon flow and a first $C_9^+$ aromatic hydrocarbon flow, obtaining a tenth flow containing $C_8$ aromatic hydrocarbons from a second $C_9^+$ aromatic hydrocarbon flow and a methylbenzene flow outside a reaction-separation system, wherein the second $C_9^+$ aromatic hydrocarbon flow is selected from the first $C_9^+$ aromatic hydrocarbon flow or a mixed flow of the first $C_9^+$ aromatic hydrocarbon flow and a $C_9^+$ aromatic hydrocarbon flow outside the reaction-separation system, obtaining an eleventh hydrocarbons flow of aromatic hydrocarbons having less than or equal to 7 carbon numbers from the seventh hydrocarbons flow and a flow H, wherein said flow H is selected from at least one of a $C_2^+$ hydrocarbons flow outside the reaction-separation system and the ninth flow; and returning said eleventh hydrocarbons flow to the oxygenate(s) flow for further reaction;

m3) separating the first liquid phase hydrocarbons flow and the second liquid phase hydrocarbons flow in a tenth separation unit by a non-precise rectification to obtain a twelfth hydrocarbons flow of aromatic hydrocarbons having less than or equal to 7 carbon numbers and a thirteenth hydrocarbons flow having more than 7 carbon numbers, and separating said thirteenth hydrocarbons flow through an eleventh separation unit to obtain the fourteenth flow containing non-aromatic hydrocarbons, a $C_8$ aromatic hydrocarbon flow and a $C_9^+$ aromatic hydrocarbon flow;

obtaining a fifteenth hydrocarbons flow of aromatic hydrocarbons having less than or equal to 7 carbon numbers from the twelfth hydrocarbons flow and a flow H, wherein said flow H is selected from at least one of $C_2^+$ hydrocarbons flow outside the reaction-separation system and the fourteenth flow; and returning said fifteenth hydrocarbons flow to the oxygenate flow for further reaction;

m4) separating the first liquid phase hydrocarbons flow and the second liquid phase hydrocarbons flow in an eighth separation unit by a non-precise rectification to obtain a twelfth hydrocarbons flow of aromatic hydrocarbons having less than or equal to 7 carbon numbers and a thirteenth hydrocarbons flow having more than 7 carbon numbers, and separating said thirteenth hydrocarbons flow through a ninth separation unit to obtain a fourteenth flow containing non-aromatic hydrocarbons, a $C_8$ aromatic hydrocarbon flow and a first $C_9^+$ aromatic hydrocarbon flow, obtaining a sixteenth flow containing $C_8$ aromatic hydrocarbons from a second $C_9^+$ aromatic hydrocarbon flow and a methylbenzene flow outside the reaction-separation system, wherein the second $C_9^+$ aromatic hydrocarbon flow is selected from the first $C_9^+$ aromatic hydrocarbon flow or a mixed flow of the first $C_9^+$ aromatic hydrocarbon flow and a $C_9^+$ aromatic hydrocarbon flow outside the reaction-separation system, obtaining a seventeenth hydrocarbons flow of aromatic hydrocarbons having less than or equal to 7 carbon numbers from the twelfth hydrocarbons flow and a flow H, wherein said flow H is selected from at least one of $C_2^+$ hydrocarbon flow outside the reaction-separation system or the fourteenth flow; and returning said seventeenth hydrocarbons flow to the oxygenate flow for further reaction.

6. The method for producing an aromatic hydrocarbon with an oxygenate as raw material according to claim 1, wherein said aromatization reactor comprises at least one of a fluidized-bed reactor, a fixed-bed reactor and a moving-bed reactor, and said transalkylation reactor and dealkylation reactor are fixed-bed reactors.

7. The method for producing an aromatic hydrocarbon with an oxygenate as raw material according to claim 1, wherein said aromatization reactor is a fluidized-bed reactor or a moving-bed reactor, optionally with different regeneration systems or with a common regeneration system.

8. The method for producing an aromatic hydrocarbon with an oxygenate as raw material according to claim 1, wherein said aromatization catalyst comprises at least one molecular sieve active component selected from ZSM-5 and ZSM-11 molecular sieves, wherein the molar ratio of silicon oxide to aluminium oxide in the molecular sieve is from 10:1 to 200:1.

9. The method for producing an aromatic hydrocarbon with an oxygenate as raw material according to claim 1, wherein said alkylation catalyst comprises at least one molecular sieve active component selected from MOR, ZSM-5 and BETA molecular sieves, and said dealkylation process may be free of catalyst or comprises oxide, molecular sieve type dealkylation catalyst.

10. The method for producing an aromatic hydrocarbon with an oxygenate as raw material according to claim 1, wherein the molecular sieve component prior to the molding of the catalyst or the catalyst supporting the modification component is subjected to a high temperature hydro-thermal treatment under conditions of a temperature of 400 to 750° C., a partial pressure of water vapor of 5 to 100%, a treatment time period of 0.5 to 120 hours.

11. The method for producing an aromatic hydrocarbon with an oxygenate as raw material according to claim 1, wherein the separation unit A comprises operation units of quenching, alkaline washing or water washing; the separation unit B comprises a pressure swing adsorption, a rectification or an adsorption; or the separation unit D comprises rectification or solvent extraction rectification.

12. The method for producing an aromatic hydrocarbon with an oxygenate as raw material according to claim 4, wherein the gas in c) comprises $H_2$, CO, $CO_2$, $N_2$ or $CH_4$.

13. The method for producing an aromatic hydrocarbon with an oxygenate as raw material according to claim 5, wherein the gas in j) comprises $H_2$, CO, $CO_2$, $N_2$ or $CH_4$.

* * * * *